(12) United States Patent
Goeders et al.

(10) Patent No.: US 9,078,886 B2
(45) Date of Patent: Jul. 14, 2015

(54) COMPOSITIONS FOR THE TREATMENT OF ADDICTION, PSYCHIATRIC DISORDERS, AND NEURODEGENERATIVE DISEASE

(75) Inventors: Nicholas E. Goeders, Shreveport, LA (US); Barbara S. Fox, Wayland, MA (US); Glenn Guerin, Shreveport, LA (US)

(73) Assignees: Embera Neurotherapeutics, Inc., Sudbury, MA (US); Board of Supervisors of Louisiana State University and Agricultural and Mechanical College, Shreveport, LA (US)

( * ) Notice: Subject to any disclaimer, the term of this patent is extended or adjusted under 35 U.S.C. 154(b) by 0 days.

(21) Appl. No.: 13/703,726

(22) PCT Filed: Jun. 16, 2011

(86) PCT No.: PCT/US2011/040647
§ 371 (c)(1),
(2), (4) Date: May 23, 2013

(87) PCT Pub. No.: WO2011/159871
PCT Pub. Date: Dec. 22, 2011

(65) Prior Publication Data
US 2013/0303523 A1    Nov. 14, 2013

Related U.S. Application Data

(60) Provisional application No. 61/355,482, filed on Jun. 16, 2010.

(51) Int. Cl.
| | |
|---|---|
| *A61K 31/445* | (2006.01) |
| *A61K 31/55* | (2006.01) |
| *A61K 31/444* | (2006.01) |
| *A61K 31/5513* | (2006.01) |
| *A61K 31/496* | (2006.01) |
| *A61K 45/06* | (2006.01) |

(52) U.S. Cl.
CPC ............. *A61K 31/444* (2013.01); *A61K 31/496* (2013.01); *A61K 31/55* (2013.01); *A61K 31/5513* (2013.01); *A61K 45/06* (2013.01)

(58) Field of Classification Search
CPC ........... A61K 31/4164; A61K 31/4178; A61K 31/4425; A61K 31/4406; A61K 31/44; A61K 31/5513; A61K 31/4174
USPC ................................................. 514/318, 218
See application file for complete search history.

(56) References Cited

U.S. PATENT DOCUMENTS

| | | | |
|---|---|---|---|
| 4,594,329 A | 6/1986 | Vale, Jr. et al. | |
| 4,605,642 A | 8/1986 | Rivier et al. | |
| 4,661,493 A | 4/1987 | Gibbs | |
| 4,814,333 A | 3/1989 | Ravaris | |
| 4,925,844 A | 5/1990 | Resch | |
| 4,942,162 A | 7/1990 | Rosenberg et al. | |
| 5,016,655 A | 5/1991 | Waddell et al. | |
| 5,456,850 A | 10/1995 | Trabitzsch et al. | |
| 5,869,474 A | 2/1999 | Goeders | |
| 6,323,312 B1 | 11/2001 | Rivier | |
| 6,326,463 B1 | 12/2001 | Rivier | |
| 2002/0078969 A1 | 6/2002 | Wastchak et al. | |
| 2003/0211157 A1 | 11/2003 | Simon | |
| 2004/0204401 A1 | 10/2004 | Migaly | |
| 2005/0037983 A1 | 2/2005 | Dinan et al. | |
| 2005/0090553 A1 | 4/2005 | Shapiro | |
| 2005/0203130 A1 | 9/2005 | Buntinx | |
| 2005/0215533 A1 | 9/2005 | Gottlieb et al. | |
| 2008/0206138 A1 | 8/2008 | Zolle | |

FOREIGN PATENT DOCUMENTS

| | | |
|---|---|---|
| EP | 1 666 468 A1 | 6/2006 |
| GB | WO 01/52833 A8 | 10/2001 |
| JP | WO 2005/061508 A1 | 7/2005 |

(Continued)

OTHER PUBLICATIONS

Ichimura, Hypothalamopituitary adrenal axis in children studied by using 11β-hydroxylase inhibitor. I. Gas-liquid chromatographic-mass spectrometric method for the determination of serum metyrapone. Pharmacokinetics and biology of metyrapone in children:, Nippon Naibunpi Gakkai Zasshi, vol. 59, No. 5, pp. 715-737 (1983), abstract.*
Arvat et al., "The Inhibitory Effect of Alprazolam, a Benzodiazepine, Overrides the Stimulatory Effect of Metyrapone-Induced Lack of Negative Cortisol Feedback on Corticotroph Secretion in Humans", The Journal of Clinical Endocrinology & Metabolism, vol. 84, No. 8, pp. 2661-2615 (1999).*
Arvat et al., "The inhibitory effect of alprazolam, a benzodiazepine, overrides the stimulatory effect of metyrapone-induced lack of negative cortisol feedback on corticotroph secretion in humans.", J. Clin. Endocrinol. & Metabol. 84:2611-2615, 1999.
Baldessarini, "Drugs and the Treatment of Psychiatric Disorder", in: Hardman et al. (Eds), Goodman & Gilman's The Pharmacological Basis of Therapeutics, McGraw-Hill, New York, pp. 399-430, 1996.

(Continued)

*Primary Examiner* — Kevin E Weddington
(74) *Attorney, Agent, or Firm* — Duane Morris LLP; Laura A. Vogel; Moreshwar B. Vaze

(57) ABSTRACT

The present invention features, inter alia, pharmaceutically acceptable compositions that include metyrapol as the sole pharmaceutically active agent; compositions that include metyrapol and at least one additional pharmaceutically active agent; compositions in which the agent targeting the HPA axis is, itself, new or modified (e.g., a bi-specific antibody designed to traverse the blood-brain barrier or a known compound redesigned by, for example, conjugation to a substance that traverses the blood-brain barrier); and compositions in which the agent targeting the HPA axis is newly formulated in such a way that it fails to significantly inhibit cortisol production in the adrenal gland. For example, the composition can be formulated to include a dosage that is too low to reduce plasma cortisol levels or formulated to preferentially affect the skin.

12 Claims, No Drawings

(56) References Cited

FOREIGN PATENT DOCUMENTS

| NZ | WO 00/54766 A1 | 9/2000 |
|---|---|---|
| WO | WO 91/00906 A1 | 1/1991 |
| WO | WO 2004/032916 A1 | 4/2004 |
| WO | WO2007056618 A1 | 5/2007 |
| WO | WO 2007/100775 A2 | 9/2007 |

OTHER PUBLICATIONS

Baumann et al., "Effects of intravenous cocaine on plasma cortisol and prolactin in human cocaine abusers.", Biol. Psych.38:751-755, 1995.
Chesley et al., "Cocaine augments peripheral benzodiazepine binding in humans.", J. Clin. Psychiatry 51:404-406, 1990.
Contoreggi et al., "Stress hormone responses to corticotropin-releasing hormone in substance abusers without severe comorbid psychiatric disease.", Biological Psychiatry, 54(9):873-878, 2003.
Crowley, "Clinical issues in cocaine abuse.", in: Fisher et al. (Eds), Cocaine: Clinical and Biobehavioral Aspects, Oxford University Press, New York, pp. 193-211, 1987.
de Souza, "Total and partial sleep deprivation in clomipramine-treated endogenous depressives.", J. Psychiatric Res. 24:111-119, 1990.
de Wit, "Priming effects with drugs and other reinforcers.", Experimental and Clinical Psychopharmacology, 4:5-10, 1996.
Di Paolo et al., "Endocrine and neurochemical actions of cocaine.", Canadian J. Physiol. Pharmacol. 67:1177-1181, 1989.
Elman et al., Acute cortisol administration triggers craving in individuals with cocaine dependence., Psychopharmacol. Bulletin 37:84-89, 2003.
Engelhardt et al., "Ketoconazole blocks cortisol secretion in man by inhibition of adrenal 11 beta-hydroxylase.", Klin. Wochenschr. 63:607-612, 1985.
Faria et al., "Phosphoramidate oligonucleotides as potent antisense molecules in cells and in vivo.", Nature Biotech. 19:40-44, 2001.
Gautier et al., "Alpha-DNA. IV: Alpha-anomeric and beta-anomeric tetrathymidylates covalently linked to intercalating oxazolopyridocarbazole. Synthesis, physicochemical properties and poly (rA) binding.", Nucleic Acids Res. 15:6625-6641, 1987.
Gawin and Ellinwood, "Cocaine dependence.", Ann. Rev. Med. 40:49-161, 1989.
Gay, J. You've come a long way, baby! Coke time for the new American lady of the Eighties., Psychoactive Drugs 13:297-318, 1981.
Ghadirian et al., "The psychotropic effects of inhibitors of steroid biosynthesis in depressed patients refractory to treatment", Biol. Psychiatry 37:369-375, 1995.
Goeders et al., "Non-contingent electric footshock facilitates the acquisition of intravenous cocaine self-administration in rats.", Psychopharmacol. 114:63-70, 1994.
Goeders and Guerin, "Role of corticosterone in intravenous cocaine self-administration in rats.", Neuroendocrinol. 64:337-348, 1996.
Goeders et al., "Effects of surgical and pharmacological adrenalectomy on the initiation and maintenance of intravenous cocaine self-administration in rats.", Brain Res. 722:145-152, 1996.
Goeders et al., "Effects of Ketoconazole on Intravenous Cocaine Self-Administration in Rats" Abstract submitted to the 58th Annual Scientific meeting of the College on Problems of Drug Dependence (CPDD), Jun. 22-27, 1996.
Goeders, "A neuroendocrine role in cocaine reinforcement.", Psychoneuroendocrinology 22:237, 1997.
Goeders et al., "Ketoconazole reduces low dose cocaine self-administration in rats.", Drug Alcohol Dependence 53:67-77, 1998.
Goeders and Guerin, "Effects of the CRH receptor antagonist CP-154,526 on intravenous cocaine self-administration in rats." Neuropsychopharmacol. 23:577-586, 2000.
Guerin et al., "Combination pharmacotherapy targeting the HPA axis and its effects on cocaine self-administration in rats", Society for Neuroscience Annual Meeting, Abstract No. 978.3, Nov. 15, 2001, San Diego, CA.
Goeders, "Stress and cocaine addiction.", J. Pharmacol. Exp. Ther. 301:785-789, 2002.
Goeders, "The HPA axis and cocaine reinforcement.", Psychoneuroendocrinology 27:13-33, 2002.
Goeders and Clampitt, "Potential role for the hypothalamo-pituitary-adrenal axis in the conditioned reinforcer-induced reinstatement of extinguished cocaine seeking in rats.", Psychopharmacol. 161:222-232, 2002.
Goeders, "The impact of stress on addiction." Eur. Neuropsychopharmacology 3:435-441, 2003.
Goeders, "Stress, Motivation, and Drug Addiction", Current Directions in Psychological Science 13:33-35, 2004.
Goeders and Goeders, "Effects of oxazepam on methamphetamine-induced conditioned place preference.", Pharmacol. Biochem. Behav. 78:185-188, 2004.
Goldstein and Volkow, "Drug addiction and its underlying neurobiological basis: neuroimaging evidence for the involvement of the frontal cortex", American Journal of Psychiatry, 159:1642-1652, 2002.
Gurkovskaya and Goeders, "Effects of CP-154,526 on responding during extinction from cocaine self-administration in rats.", Eur. J. Pharmacol. 432:53-56, 2001.
Haleem et al., "Adaptation of female rats to stress: shift to male pattern by inhibition of corticosterone synthesis.", Brain Res. 458:339-347, 1988.
Haynes, in: Gilman et al. (Eds), "Adrenocorticotropic Hormone; Adrenocortical Steroids and Their Synthetic Analogs; Inhibitors of the Synthesis and Actions of Adrenocortical Hormones", in The Pharmacological Basis of Therapeutics, eighth edition, Pergamon Press, New York, pp. 1431-1462, 1990.
Heesch et al., "Effects of cocaine on cortisol secretion in humans.", Am. J. Med. Sci. 310:61-64, 1995.
Helene, "The anti-gene strategy: control of gene expression by triplex-forming-oligonucleotides.", Anticancer Drug Des. 6:569-584, 1991.
Helene, "Control of gene expression by triple helix-forming oligonucleotides. The antigene strategy.", Ann. N.Y. Acad. Sci. 660:27-36, 1992.
Hyrup et al., "Peptide nucleic acids (PNA): synthesis, properties and potential applications.", Bioorganic & Medicinal Chemistry 4:5-23, 1996.
Inoue et al., "Synthesis and hybridization studies on two complementary nona(2'-O-methyl)ribonucleotides.", Nucleic Acids Res. 15:6131-6148, 1987.
Inoue et al., "Sequence-dependent hydrolysis of RNA using modified oligonucleotide splints and RNase H.", Febs Lett. 215:327-330, 1987.
Javaid et al., "Peripheral benzodiazepine receptors are decreased during cocaine withdrawal in humans.", Biol. Psychiatry 36:44-50, 1994.
Joels et al., "Mineralocorticoid and glucocorticoid receptors in the brain. Implications for ion permeability and transmitter systems.", Prog. Neurobiol. 43:1-36, 1994.
Kleber, "Pharmacotherapy, Current and Potential, for the Treatment of Cocaine Dependence", Clinical Neuropharmacology 18(Suppl. 1):S96-S109, 1995.
Lamon and Alonzo, "Stress among males recovering from substance abuse.", Addict. Behav. 22:195-205, 1997.
Licinio et al., "The hypothalamic-pituitary-adrenal axis in anorexia nervosa." Psychiatry Res. 62:75-83, 1996.
Loose et al., "Ketoconazole binds to glucocorticoid receptors and exhibits glucocorticoid antagonist activity in cultured cells." J. Clin. Invest. 72:404-408, 1983.
Maher, "DNA triple-helix formation: an approach to artificial gene repressors?", Bioassays 14:807-815, 1992.
Mantsch et al., "Corticosterone facilitates the acquisition of cocaine self-administration in rats: opposite effects of the type II glucocorticoid receptor agonist dexamethasone.", J. Pharmacol. Exp. Ther. 287: 72-80, 1998.
Mantsch and Goeders, "Ketoconazole blocks the stress-induced reinstatement of cocaine-seeking behavior in rats: relationship to the discriminative stimulus effects of cocaine.", Psychopharmacology 142: 399-407, 1999.

(56) References Cited

OTHER PUBLICATIONS

Mantsch and Goeders, Ketoconazole does not block cocaine discrimination or the cocaine-induced reinstatement of cocaine-seeking behavior, Pharmacol. Biochem. and Behavior 64:65-73, 1999.
Guerin and Goeders, "Effects of metyrapol on cocaine self-administration in rats" Society for Neuroscience, annual meeting abstract, Nov. 18, 2008.
Supplementary European search report in the European application No. EP 11 79 6418, Nov. 11, 2013.
European search opinion, in the European application No. EP 11 79 6418, Nov. 11, 2013.
Ichimura, Hypothalamopituitary adrenal axis in children studied by using 11β-hydroxylase inhibitor. I. Gas-liquid chromatographic-mass spectrometric method for the determination of serum metyrapone. Pharmacokinetics and biology of metyrapone in children:, Nippon Naibunpi Gakkai Zasshi, 59(5): 715-737, 1983.
de Lind van Wijngaarden et al., "High Prevalence of Central Adrenal Insufficiency in Patients with Prader-Willi Syndrome" J Clin Endocrinol Metab. 93(5):1649-54, 2008.
Mantsch and Goeders, "Effects of cocaine self-administration on plasma corticosterone in rats: relationship to hippocampal type II glucocorticoid receptors.", Prog. Neuropsychopharmacol. Biol. Psyc. 24:633-646, 2000.
Mendelson et al., "Buprenorphine attenuates the effects of cocaine on adrenocorticotropin (ACTH) secretion and mood states in man.", Neuropsychopharmacol. 7:157-162, 1992.
Mendelson et al., "Effects of low- and high-nicotine cigarette smoking on mood states and the HPA axis in men.", Neuropsychopharmacol. 30:1751-1763, 2005.
Murphy et al., "Response to steroid suppression in major depression resistant to antidepressant therapy.", J. Clin. Psychopharmacol. 11:121-126, 1991.
Patel et al., "Endocannabinoid signaling negatively modulates stress-induced activation of the hypothalamic-pituitary-adrenal axis.", Endocrinol. 145:5431-5438, 2004.
Peltier et al.,"Effects of saline substitution on responding and plasma corticosterone in rats trained to self-administer different doses of cocaine.", J. Pharmacol. Exp. Ther. 299:114-120, 2001.
Perault-Staub and Staub, "Thyroid function and plasma phosphate level in rat.", Endocrinol., 90: 558-562, 1972.
Perry-O'Keefe et al., "Peptide nucleic acid pre-gel hybridization: an alternative to southern hybridization.", Proc. Natl. Acad. Sci. USA 93:14670-14675, 1996.
Rivier et al., "Synthetic competitive antagonists of corticotropin-releasing factor: effect on ACTH secretion in the rat.", Science 224:889, 1984.
Shaham et al., "Stress-induced relapse to heroin and cocaine seeking in rats: a review.", Brain Res. Rev. 33:13-33, 2000.
Sinha, Psychopharmacol. "How does stress increase risk of drug abuse and relapse?", 158:343-359, 2001.
Smagin and Goeders, "Effects of acute and chronic ketoconazole administration on hypothalamo-pituitary-adrenal axis activity and brain corticotropin-releasing hormone.", Psychoneuroendocrinology 29:1223-1228, 2004.
Sonino, in: Agarwal (Ed), "Inhibition of Adrenal Steroid Biosynthesis by Metyrapone", in "Hormone Antagonists", Walter de Gruyter, Berlin, pp. 421-429, 1982.
Sonino, "The use of ketoconazole as an inhibitor of steroid production.", New Engl. J. Med. 317:812-818, 1987.
Stewart, "Pathways to relapse: the neurobiology of drug- and stress-induced relapse to drug-taking.", J. Psychiatr. Neurosci. 25:125-136, 2000.
Tanaka et al., "Sequence-specific interaction of alpha-beta-anomeric double-stranded DNA with the p50 subunit of NF kappa B: application to the decoy approach.", Nucl. Acids Res. 22:3069-3074, 1994.
Tarr and Macklin, _Cocaine., Pediatric Clinics of North America 34:319-331, 1987.
Tasker, "Endogenous cannabinoids take the edge off neuroendocrine responses to stress.", Endocrinol. 145:5429-5430, 2004.
Thienpont et al., "Ketoconazole—a new broad spectrum orally active antimycotic.", Experientia 35:606-607, May 15, 1979.
Thomas et al., "Comparative receptor binding analyses of cannabinoid agonists and antagonists.", J. Pharmacol. Exp. Ther. 285:285-292, 1998.
Toulmé, "New Candidates for True Antisense", Nature Biotech., 19:17-18, 2001.
Wolkowitz et al., "Ketoconazole administration in hypercortisolemic depression.", Am. J. Psychiatry 150:810-812, 1993.
Zhang and Barrett, "Interactions of corticotropin-releasing factor with antidepressant and anxiolytic drugs: behavioral studies with pigeons.", Biol. Psychiatry 27:953-967, 1990.
Reuter et al., The role of cortisol suppression on craving for and satisfaction from nicotine in high and low impulsive subjects., Human Psychopharmacology Clinical and Experimental 17(5):213-24, 2002.
International Search Report for PCT/US2011/040647, Apr. 19, 2012.
(IB/373) International Preliminary Report on Patentability Chapter I for PCT/US2011/040647, Dec. 19, 2012.
Written Opinion of the International Search Authority for PCT/US2011/040647, Dec. 16, 2012.

* cited by examiner

COMPOSITIONS FOR THE TREATMENT OF ADDICTION, PSYCHIATRIC DISORDERS, AND NEURODEGENERATIVE DISEASE

CROSS-REFERENCE TO RELATED APPLICATIONS

This application claims the benefit of the filing date of U.S. Provisional Application No. 61/355,482, which was filed Jun. 16, 2010. In any jurisdiction where incorporating material by reference is permitted, the entire content of U.S. Provisional Application No. 61/355,482 is hereby incorporated by reference herein.

GOVERNMENT RIGHTS STATEMENT

This invention was made with government support under United States Public Health Service grant DA06013 awarded by the National Institute on Drug Abuse. The government has certain rights in the invention.

TECHNICAL FIELD

This invention relates to compositions and methods for treating addiction, other disorders, including psychiatric conditions that may or may not be related to addiction (e.g., anxiety and post-traumatic stress disorder), and neurodegenerative disease. More particularly, the invention includes pharmaceutical compositions that include one or more active agents that positively influence behavior in the context of addiction, reducing the risk of relapse. In some embodiments, the pharmaceutical compositions are formulated so they do not significantly inhibit plasma cortisol levels upon administration to a patient, and the active agent(s) can be constructed specifically to transgress the blood-brain barrier.

SUMMARY OF THE INVENTION

We have previously conducted studies indicating that certain types of therapeutic agents can be used in combination to treat addiction to a substance, such as a drug, or to an activity, such as gambling. Based on those prior studies, we described combination pharmacotherapies that would provide a benefit to a patient (e.g., a reduction in the likelihood of relapse), and we hypothesized that those pharmacotherapies would attenuate activity within the HPA axis (e.g., by attenuating cue-induced increases in activity within the HPA axis) (see U.S. Application Publication No. 2009/0203669). Among the compositions previously described were those including at least one active ingredient that targets the hypothalamo-pituitary-adrenal (HPA) axis (a "first" active agent) and at least one active ingredient that targets the prefrontal cortex (a "second" active agent). For example, the compositions could include a first active agent that reduces the expression or activity of CRH, ACTH and/or cortisol and a second active agent that decreases activity in the prefrontal cortex (e.g., cue-induced activity dampened by the inhibitory neurotransmitter GABA). While our ongoing work supports the therapies we previously described, we have now conducted studies indicating that positive outcomes can be achieved with pharmaceutical compositions that do not significantly lower the levels of plasma cortisol. We have further conceived pharmaceutical compositions that include metyrapol, which may be used alone or in combination with additional active agents; we have further conceived pharmaceutically active agents that selectively inhibit detrimental activity in tissues other than the cortisol-producing adrenal gland (e.g., in the brain); and we have determined that additional conditions (e.g., neurodegenerative disease) can be treated not only with the compositions described herein but also with the pharmaceutical compositions described previously in U.S. Application Publication No. 2009/0203669. Thus, the present invention features, inter alia, pharmaceutically acceptable compositions that include metyrapol as the sole pharmaceutically active agent; compositions that include metyrapol and at least one additional pharmaceutically active agent; compositions in which the agent targeting the HPA axis is, itself, new or modified (e.g., a bi-specific antibody designed to traverse the blood-brain barrier or a known compound redesigned by, for example, conjugation to a substance that traverses the blood-brain barrier); and compositions in which the agent targeting the HPA axis is newly formulated in such a way that it fails to significantly inhibit cortisol production in the adrenal gland. For example, the composition can be formulated to include a dosage that is too low to reduce plasma cortisol levels or formulated to preferentially affect the skin. For example, one can formulate an agent that targets the HPA axis in a topical formulation for application to the skin (e.g., in a gel, cream, ointment, lotion, or salve or a formulation suitable for release from a transdermal patch). In addition to the skin and brain, the present compositions can be formulated to target the intestine or thymus. We use the term "conjugated" to broadly refer to any physical attachment; two agents that are joined through a covalent bond or an ionic bond, for example, are conjugated.

Accordingly, the invention features pharmaceutical compositions that include metyrapol, either as the sole active pharmaceutical agent or as one of a combination of (e.g., one of two or three) active agents. While formulations are discussed further below, we note here that such a composition can be formulated for oral, topical, intravenous, or subcutaneous administration to a patient, and one or more of the active agents can be conjugated to a peptide-based agent (e.g., an antibody) that facilitates its transport across the blood-brain barrier. Where the pharmaceutical composition includes metyrapol and a second pharmaceutically active agent, the second agent can be an agent that increases the expression or activity of GABA (gamma-aminobutyric acid); is a GABA mimic; or inhibits GABA metabolism in the patient. In any configuration, the metyrapol can be present in a unit dosage form in an amount insufficient to reduce plasma levels of cortisol in the patient. (In other embodiments, discussed further below, the first agent, such as metyrapol, can be present in a unit dosage form in an amount that is sufficient to reduce plasma levels of cortisol in the patient.)

The metyrapol-containing composition discussed immediately above and any of the other compositions described herein as aspects of the present invention can be prepared in unit dosage form. In such form, the composition is subdivided into unit doses containing appropriate quantities of the active component (e.g., pharmaceutically effective doses). The unit dosage form can be essentially any discrete unit known in the pharmaceutical industry, such as a capsule, tablet, cachet, lozenge, gel-cap, patch (e.g., transdermal patch), powder prepared, for example, for expulsion from an aerosol inhaler, or the like. Practically, the unit dosage forms can be packaged together, and may be included in a number representing a course of treatment.

Agents that target the HPA axis, including meytrapol, can be conjugated to an agent or moiety that facilitates movement of the agent across the blood-brain barrier. Alternatively, or in addition, the pharmaceutical compositions can include an efflux inhibitor that helps maintain levels of the active agent (e.g., metyrapol) in the brain once the active reaches the brain.

While excipients are described further below, we note here that any of the present pharmaceutical compositions can include one or more of: a polyethylene glycol, glycerin, and a gelatin.

The invention also features pharmaceutical compositions that include a first agent that targets the hypothalamo-pituitary-adrenal (HPA) axis but does not significantly lower plasma cortisol and a second agent that targets the prefrontal cortex. Cortisol levels can be readily measured by techniques well known in the art, and are recognized to fluctuate (e.g., over the course of a 24-hour period). As one of ordinary skill in the art would recognize, cortisol levels (e.g., in a treated versus an untreated patient) should therefore be compared at similar times of the day or under otherwise normalized conditions. In the context of the present compositions, an agent significantly lowers plasma cortisol when, for example, plasma cortisol levels in at least or about 70% of a treated population (e.g., in at least or about 75%, 80%, 85%, 90%, or 95%) fall below about 5 µg/dL (e.g., below about 5.0, 4.5, 4.0, 3.5, 3.0, 2.5, or 2.0 µg/dl in a blood sample obtained in the early morning (e.g., around 8 a.m.)).

The agent that inhibits the HPA axis can be an agent that inhibits the expression or activity of corticotropin-releasing hormone (CRH) or adrenocorticotropic hormone (ACTH). While such agents are described in further detail below, we not here that the "first" agent can be metyrapone (Metopirone®), an active metabolite thereof (e.g., metyrapol), or ketoconazole (Nizoral®). Similarly, agents that target the prefrontal cortex are described in further detail below and include benzodiazepines, such as oxazepam and chlordiazepoxide.

Within the composition described above, the active agents can be formulated in a unit dosage form, and the effective amount of the agent that targets the HPA axis can be an amount insufficient to reduce plasma levels of cortisol in the patient. Within the compositions of the invention, the first agent and/or the second agent can be conjugated to a moiety that facilitates movement across the blood-brain barrier. Alternatively, or in addition, the compositions can include an efflux inhibitor that helps maintain the level of the first agent and/or the second agent in the brain. Useful excipients include polyethylene glycol, glycerin, and gelatin.

The methods of treatment include methods of treating a patient who is suffering from a disorder associated with aberrant activity in the HPA axis, and the method can include administering, to the patient, a therapeutically effective amount of a composition described herein. The invention includes use of the compositions in the preparation of a medicament, and use in the preparation of a medicament for treating a disorder associated with aberrant activity in the HPA axis, including the specific disorders described herein. Any of the methods of the invention can include the step of identifying a patient in need of treatment, and the patient can be a human patient.

Disorders amenable to treatment include addiction, anxiety, obesity (in some instances as the result of an addiction to food), depression, premenstrual dysphoric syndrome, schizophrenia, and neurodegenerative disease. The neurodegenerative disease can be Alzheimer's disease, Parkinson's disease, Huntington's disease, or amyotrophic lateral sclerosis.

The compositions of the invention are not limited to those that function by any particular cellular or molecular mechanism. However, with respect to addiction, we selected agents and combinations of agents with the goal of blocking the ability of environmental cues to produce a conditioned activation of the HPA axis and sympathetic nervous system that reminds an abstinent addict about his or her drug of choice, which leads to craving and relapse. Thus, the compositions include those that reduce the ability of conditioned stimuli to increase activity in the HPA axis and sympathetic nervous system but do not reduce or significantly reduce basal activity. Our adrenalectomy data suggest that the effects of metyrapone combined with oxazepam, at least, are mediated above the level of the adrenal gland, quite possibly in the prefrontal cortex, where GABA is active.

Unless the context indicates otherwise, we use the term "agent" to broadly refer to any substance that affects a target molecule (e.g., a target such as an enzyme, a ligand, or the receptor to which the ligand binds) or a target region of the body (e.g., the brain, skin, or a gland or organ of the endocrine system) in a clinically beneficial way (e.g., to inhibit HPA or stress axis activation following a patient's exposure to one or more conditioned environmental cues). For example, we may refer to chemical compounds such as metyrapone (Metopirone®) and oxazepam as "agents." We may also use the term "compound" to refer to conventional chemical compounds (e.g., small organic or inorganic molecules). The "agent" may also be a protein or protein-based molecule (e.g., a mutant ligand or an antibody) or a nucleic acid or nucleic acid-based entity (e.g., antisense oligonucleotides, RNA molecules that mediate RNAi, and vectors useful for their delivery). For example, we may refer to an antibody that specifically binds and alters (e.g., inhibits) the activity of CRH (e.g., a human or humanized anti-CRH antibody) or to a nucleic acid (e.g., an siRNA or shRNA) that specifically interacts with, and inhibits translation of, an RNA encoding CRH as an "agent" that inhibits CRH. CRH is only one of the molecules that can be targeted; ACTH, cortisol (in some embodiments), and GABA can also be targeted by the types of agents discussed here in reference to CHR. Agents useful in the methods of the invention include antagonists of a cortisol receptor (preliminary results indicate that corticosterone is elevated in an animal model of addiction) and, as noted, methods of treating addiction and the other conditions described herein can be carried out by administering pharmaceutical compositions that include metyrapone, metyrapol or another agent that targets the HPA axis without depressing plasma cortisol levels.

As noted, an agent that targets the HPA axis (e.g., the first agent in a dual- or multi-agent pharmaceutical composition) may be delivered at a dosage that does not significantly lower plasma cortisol levels (and instances in which such compositions may be prescribed are discussed further below). It is well within the abilities of one of ordinary skill in the art to determine such dosages, as cortisol levels can be readily measured in blood samples. Our evidence to date suggests that compositions including 0.5-50.0 mg/kg of a first agent (e.g., metyrapone or metyrapol) administered orally, would achieve such a result. It is well known in the art that circulating dosages vary depending on the route of administration and other considerations, and other dosages may be appropriate and effective. As noted, the first agent can also be administered in a manner that facilitates traversal of the blood-brain barrier, and methods and agents to facilitate delivery of compounds to the brain are known in the art and discussed further below.

When an agent "targets" a tissue (e.g., within the nervous system, skin, or endocrine system), it affects the activity of cells or a biological process within that area in such a way as to confer a benefit on the patient. For example, where a patient is addicted to a substance or activity, the benefit can be a reduction in the patient's engagement with that substance or activity. For example, the patient may use the substance or carry out the activity less frequently or to a lesser extent than one would expect in the absence of treatment or to a lesser extent than prior to treatment. Thus, the benefit can be characterized as a reduction in the risk of relapse, even in the presence of conditioned environmental cues. The clinical benefit can be subjective in that patients may report a reduction in their craving for a substance or activity. While treatment is described further below, we note here that the compounds and methods of the invention can be used to promote abstinence or periods of abstinence that are longer than one would expect in the absence of treatment. Thus, addictive behaviors, such as drug use, would occur less frequently. With respect to the other conditions amenable to treatment, the benefit can be an improvement in one or more of the signs or symptoms associated with the condition. For example, where Alzheimer's disease is being treated, the benefit can be improved cognitive function as evidenced, for example, by improved memory or ability to converse with others. Where Parkinson's Disease, Huntington's Disease, or ALS is being treated, the benefit can be, for example, improved motor skills or improved speech (or a lessening of the rate of impairment of the patient's motor skills and/or speech).

At least some of the agents that can be included in the present compositions, including cortisol synthesis inhibitors and benzodiazepines, have potential side effects. For example, cortisol synthesis inhibitors have the potential to produce adrenal insufficiency, and benzodiazepines have the potential for dependence and abuse, making them problematic in the treatment of addiction (Chouinary, *J. Clin. Psychiatry* 65 Suppl. 5:7-12, 2004; Lilja et al., *Subst. Use Misuse* 36(9-10):1213-1231, 2001; O'Brien, *J. Clin. Psychiatry* 66 Suppl. 2:28-33, 2005). To address these concerns in the context of the present invention, we provide, in at least some embodiments, compositions containing reduced dosage levels and/or a combination of agents that affect the activity of the HPA axis (or stress axis) by acting through different mechanisms than those triggered by conventional administration or on different targets (e.g., tissues other than the adrenal cortex). Thus, in some embodiments, the present compositions and methods deliver agents at doses that have little or no effect when administered alone. This minimizes potential toxic and unwanted side effects while maintaining treatment efficacy. We have demonstrated, in a rat model of cocaine dependence, that combinations of metyrapone and oxazepam, administered at doses that were ineffective when delivered singly, resulted in dose-related decreases in cocaine self-administration in rats (Goeders and Guerin, *Pharmacol. Biochem. Behav.* 91(1):181-189, 2008). These same combinations did not affect food-maintained responding during the same sessions. Unlike the prior compositions, those described here for the treatment of addiction include those having a first agent (e.g., metyrapone, metyrapol, or another agent that targets the HPA axis) formulated such that circulating plasma levels of cortisol are not significantly reduced.

The details of one or more embodiments of the invention are set forth in the description below. Other features, objects, and advantages of the invention will be apparent from the detailed description and the claims.

DETAILED DESCRIPTION

The present invention includes various compositions and methods, the compositions including one or more pharmaceutically active agents for the treatment of addiction and other disorders described herein, such as anxiety, depression, premenstrual dysphoric disorder, and neurodegenerative disease. We first describe in further detail the active pharmaceutical agents in the present compositions.

Generally, an agent included in the present compositions can be one that is currently available but not currently formulated as described herein and/or not currently prescribed for treating a condition described herein. For example, metyrapone, which is known in the art and commonly used to diagnose malfunction of the adrenal glands, can be incorporated in the present compositions and administered in the treatment regimes described herein. Alternatively, one or more of the agents can be newly generated in accordance with the teachings herein and information readily available in the art. For example, an antisense oligonucleotide or an RNA molecule that mediates RNAi can be produced given the sequence(s) of the target(s) discovered (e.g., CRH, ACTH, or β adrenergic receptors in the sympathetic nervous system). The sequences of these targets are known or readily available to one of ordinary skill in the art, as are methods for making antisense oligonucleotides and RNA molecules that mediate RNAi. Other useful agents, whether previously available or newly made, include antibodies that selectively bind a ligand identified herein (e.g., CRH or ACTH) or a receptor activated in response to conditioned environmental cues (e.g., a receptor for CRH, ACTH, cortisol, or GABA). Where the target, such as a cortisol receptor, is localized to the cytoplasm, the agent can be an intrabody. We use the term "selectively bind(s)" as is conventional in the field of antibody therapeutics to indicate that the antibody agent exhibits specificity toward its target, binding the target with an affinity greater than the affinity with which it binds a non-target and eliciting a beneficial outcome for the patient. For example, an antibody suitable for inclusion in the present compositions would bind, for example, CRH with an affinity greater than (and preferably much greater than) it would bind a peptide hormone other than CRH.

The agents can be categorized in various ways, and the compositions of the invention that include at least two active pharmaceutical agents can include two or more agents of the same or different types. For example, the agents can be categorized as chemical compounds (e.g., metyrapone and topiramate); as protein or protein-based molecules, such as mutant ligands (e.g., a ligand that binds but does not activate or fully activate its cognate receptor) or antibodies; or as nucleic acids or nucleic acid-based entities, such as antisense oligonucleotides or RNA molecules that mediate RNAi. Thus, the compositions of the invention can include two or more distinct chemical compounds; two or more distinct protein or protein-based molecules; or two or more distinct nucleic acids or nucleic acid-based entities. Alternatively, the compositions can include two different types of agents. The methods by which patients are treated can similarly include administration of two or more distinct chemical compounds; two or more distinct proteins or protein-based molecules; two or more distinct nucleic acids or nucleic acid-based entities; or any combination of agents of these various types (e.g., a protein and a nucleic acid).

In a first aspect, the invention features compositions in which metyrapol is the sole active pharmaceutical agent (for ease of reading, where there is a sole active pharmaceutical agent we may refer simply to "the sole active" or "the active" and where a composition includes more than one active pharmaceutical agent, we may refer simply to the "actives"). Metyrapol is a metabolite of metyrapone and can be synthesized from metyrapone. Based on precedent in the literature for this type of chemistry transformation, we expect one synthesis reaction to entail sodium borohydride reduction of the ketone functionality of metyrapone, producing a racemic mixture of metyrapol. In some embodiments, the compositions include metyrapol as the sole active, and the compositions are formulated such that plasma cortisol levels are lowered in a patient to whom the composition has been administered. In other embodiments, the compositions include metyrapol as the sole active, and the compositions are formulated such that plasma cortisol levels are not lowered following administration. Where plasma cortisol levels are maintained, metyrapol can be included at dosages that are too low to have an effect on circulating levels or formulated or applied in such a way that the metyrapol selectively affects tissues other than the adrenal glands (e.g., the brain). Dosages and formulations are discussed in further detail below. We note here that oral and topical formulations can be made and used with particular ease. Further, any of the actives described herein, including metyrapol, can be conjugated to a protein or other moiety that facilitates transport across the blood-brain barrier. While less convenient, these conjugates and other protein-based therapeutics such as the bi-specific antibodies discussed below can also be formulated for intravenous or intraperitoneal administration.

In a second aspect, the invention features compositions in which metyrapol is combined with one or more additional active pharmaceutical agents. For example, metyrapol can be included as one of two or more actives (e.g., metyrapol can be included or administered as one of three actives). The additional agent (e.g., the "second" agent) can target the prefrontal cortex or the sympathetic nervous system. Where there are three actives, the first can be metyrapol, the second can target the prefrontal cortex, and the third can target the sympathetic nervous system. Thus, the present compositions can include metyrapol and an agent that targets the prefrontal cortex; metyrapol and an agent that targets the sympathetic nervous system; or metyrapol, an agent that targets the prefrontal cortex, and an agent that targets the sympathetic nervous system. These agents are discussed further below. Compositions including metyrapol and one or more additional active agents can be formulated such that they either lower or fail to lower plasma cortisol levels, and dosages and formulations useful in achieving these outcomes are described further below. Regardless of whether or not plasma cortisol levels are lowered in the course of treatment, metyrapol and/or the agent targeting the prefrontal cortex can be conjugated to a protein or other moiety that facilitates transport across the blood-brain barrier.

For the sake of added clarity, through the first and second aspects, the invention includes compositions in which: metyrapol is the sole active in a composition that is formulated such that plasma cortisol levels are lowered; metyrapol is the sole active in a composition that is formulated such that plasma cortisol levels are not significantly lowered; metyrapol is one of two or more actives in a composition formulated such that plasma cortisol levels are lowered; and metyrapol is one of two or more actives in a composition formulated such that plasma cortisol levels are not significantly lowered.

In a third aspect, the invention features compositions (e.g., pharmaceutical compositions) that include, as the sole active pharmaceutical agent, an agent that targets the HPA axis, and these compositions can be formulated such that plasma cortisol levels are not lowered in a patient to whom the composition is administered. Regardless of whether or not plasma cortisol levels are lowered, the agent that targets the HPA axis can be conjugated to a protein or other moiety that facilitates its transport across the blood-brain barrier or increases its availability to tissues other than the adrenal gland (e.g., the skin, intestine, and thymus). More specifically, the sole active in these compositions can be an agent that inhibits CRH or ACTH. Agents that inhibit CRH include agents that inhibit CRH expression (e.g., nucleic acids); agents that inhibit the formation of CRH from a pre- or prepro-hormone; agents that inhibit CRH production or secretion by way of participation in a negative feedback loop (e.g., cortisol); antibodies that specifically bind to and inhibit CRH; CRH receptor antagonists (e.g., proteins, including mutant CRH, antibodies and intrabodies, that bind a CRH receptor (e.g., CRH-1, CRH-2a, CRH-2b, or CHR-2g) and inhibit signal transduction or act intracellularly to inhibit the second messengers normally generated in response to CRH receptor binding; chemical compounds (e.g., small molecules) that inhibit the expression, secretion, or activity of CRH or the CRH receptor (e.g., compounds that inhibit the ability of CRH to bind cognate receptors in the pituitary (e.g., pexacerfont (developed by Bristol-Myers Squibb as BMS-562,086) and antialarmin)); and agents that facilitate CRH metabolism. The invention encompass these agents when conjugated to a protein or other moiety that facilitates their transport across the blood-brain barrier, pharmaceutical compositions that contain them, and pharmaceutical compositions that include an agent that is not joined to the active (i.e., not conjugated to the active) but is otherwise a part of the composition that facilitates passage across the blood-brain barrier or retention of the active in the brain.

Agents that inhibit ACTH include agents that inhibit ACTH expression (e.g., nucleic acids); agents that inhibit ACTH production or secretion by way of participation in a negative feedback loop (e.g., cortisol); antibodies that specifically bind to and inhibit ACTH; ACTH receptor antagonists (e.g., proteins that bind the ACTH receptor and inhibit signal transduction or that act intracellularly to inhibit the second messengers normally generated in response to ACTH receptor binding); chemical compounds that inhibit the expression, secretion, or activity of ACTH or the ACTH receptor (e.g., compounds that inhibit the ability of ACTH to bind cognate receptors in the adrenal gland); and agents that facilitate ACTH metabolism. Because of the existing negative feedback loop, one can administer ACTH per se; administering an amount sufficient to trigger feedback inhibition or down-regulate the ACTH receptor results in an inhibition of ACTH. These agents may be delivered at a dose, by a route of administration, or formulated such that they do not result in a significant lowering of plasma cortisol.

More specifically, agents that inhibit CRH include [Met18, Lys23, Glu27,29,40, Ala32,41, Leu33,36,38] CRF9-41, which is abbreviated as alpha-helical CRF(9-41) and has the sequence Asp-Leu-Thr-Phe-His-Leu-Leu-Arg-Glu-Met-Leu-Glu-Met-Ala-Lys-Ala-Glu-Gln-Glu-Ala-Glu-Gln-Ala-Ala-Leu-Asn-Arg-Leu-Leu-Leu-Glu-Glu-Ala (SEQ ID NO:1)) and biologically active fragments or variants thereof (Rivier et al., *Science* 224:889, 1984) (e.g., CRF(8-41). Another agent that inhibits CRH is [D-Phe12, Nle21,38, (αMeLeu37)] CRF(12-41), which is abbreviated as D-Phe CRF12-41, and biologically active fragments and variants thereof. Other agents that inhibit CRH include astressin or astressin-B; CP-154,526; NB127914, antalarmin; CRA1000; CRA1001, and antisauvagine-30.

Agents that target the HPA axis also include the compounds metyrapone and metyrapol (a metabolite of metyrapone), ketoconazole, aminoglutethamide, substance P antagonists, and vasopressin inhibitors. Metyrapone inhibits cortisol and corticosterone synthesis (in humans and rats, respectively) by inhibiting the 11β-hydroxylation step in the synthesis of adrenocorticosteroids (Sonino, In: Agarwal (Ed), Hormone antagonists, Walter de Gruyter, Berlin, pp 421-429, 1982; Haleem et al., *Brain Res.* 458, 339-347, 1988; Haynes, In: Gilman et al. (Eds), The Pharmacological Basis of Therapeutics, eighth edition, Pergamon Press, New York, pp. 1431-1462, 1990). We have investigated the effects of the corticosterone synthesis inhibitor metyrapone and ketoconazole on cocaine self-administration in rats. Pretreatment with metyrapone can result in significant dose-related decreases in both plasma corticosterone and ongoing cocaine self-administration (see also Goeders et al., *Brain Res.* 722:145-152, 1996).

Ketoconazole is an oral antimycotic agent with a broad spectrum of activity that is used in the treatment of fungal disease (Sonino, In: Agarwal (Ed), Hormone Antagonists, Walter de Gruyter, Berlin, pp 421-429, 1982; Thienpont et al., *Experientia* 35:606-607, 1979). This drug also inhibits the 11β-hydroxylation and 18-hydroxylation steps in the synthesis of adrenocorticosteroids (Engelhardt et al., *Klin. Wochenschr.* 63:607-612, 1985) and may also function as a glucocorticoid receptor antagonist (Loose et al., *J. Clin. Invest.* 72:404-408, 1983). Furthermore, clinical trials have suggested that ketoconazole (as well as metyrapone) is effective in the treatment of hypercortisolemic depression that is resistant to standard antidepressant therapy (Ghadirian et al., *Biol. Psychiatry* 37:369-375, 1995; Murphy et al., *J. Clin. Psychopharmacol.* 11:121-126, 1991; Wolkowitz et al., *Am. J. Psychiatry* 150:810-812, 1993).

Other agents that target the HPA axis, probably by inhibiting 11-beta-hydroxylase, include etomidate and analoges thereof as described in Zolle et al. (*J. Med. Chem.* 51:7652, 2008) and AY-9944, as described in Givner et al. (*Nature* 203:317, 1964). These agents can be employed in the present compositions and methods as described herein.

As noted, the invention includes nucleic acid- and protein-based therapeutics that, by virtue of their own nature, by conjugation to another substance, or by the manner of formulation, achieve preferential access to target tissues such as the hypothalamus, where CRH is produced, and the pituitary gland, where ACTH is produced. These therapeutics are among those useful as agents that target the HPA axis, and they are discussed further below.

For the sake of added clarity, through the third aspect, the invention includes compositions in which the sole active is an agent that inhibits the expression or activity a signaling molecule in the HPA axis (CRH, ACTH, or cortisol) or the expression or activity of a receptor bound by such a signaling molecule. As some of these agents are presently known and used in the art, we wish to emphasize that the known agents (e.g., metyrapone and ketoconazole) are formulated differently in accordance with the present invention; they are formulated at a dosage that is too low to reduce plasma cortisol levels and/or in a way that preferentially delivers them to a suitable target tissue other than the adrenal gland (e.g., they are formulated as topical preparations or conjugated to a protein or other moiety that facilitates their transport across the blood-brain barrier, biasing their delivery to the brain rather than the adrenal gland).

In a fourth aspect, the invention features compositions (e.g., pharmaceutical compositions) that include a first agent that targets the HPA axis and a second agent that targets the prefrontal cortex. Moreover, the compositions can be formulated such that they do not significantly lower plasma cortisol levels. Regardless of whether or not plasma cortisol levels are affected, either or both of the first and second agents can be conjugated to a protein or other moiety that facilitates transport across the blood-brain barrier. The first agent that targets the HPA axis can be any of those described herein (for example, metyrapol, any of the agents described above in the context of the third aspect of the invention, or any of the nucleic acids or antibodies described in more detail below).

The second active agent can target the prefrontal cortex by increasing the expression or activity of gamma-aminobutyric acid (GABA); mimicking GABA; or inhibiting GABA metabolism. GABA is an inhibitory neurotransmitter that hyperpolarizes the inhibited neuron following receptor binding. This binding opens chloride and potassium channels, either directly or indirectly. Activated ionotropic receptors are ion channels themselves while the metabotropic receptors are G protein-coupled receptors that activate ion channels via the intermediary G proteins. Either type of receptor can be activated by an agent that mimics GABA and thereby targets the prefrontal cortex. Benzodiazepines (e.g., oxazepam), which are widely prescribed for management of anxiety, are one class of drugs useful in modulating GABA receptors. It is believed that benzodiazepines bind GABA receptors, making them more efficient by increasing the frequency with which the chloride channel opens when GABA binds to its own site on the receptor. The resulting increase in intracellular chloride ions in post-synaptic neurons hyperpolarizes the neuron, making it less excitable. Barbiturates produce similar effects by binding another site on the GABA receptor and are useful as agents that target the prefrontal cortex.

Other agents can act by increasing GABA synthesis. For example, nucleic acids encoding the synthetic enzyme L-glutamic acid decarboxylase, or a biologically active fragment or other mutant thereof, can be administered to a patient who is likely to benefit from the methods described herein (e.g., a patient who has demonstrated or who has been diagnosed as having an addiction (other patients amenable to treatment are described further below)). An agent that directly or indirectly stimulates GABA in the prefrontal cortex may do so by directly or indirectly increasing the synthesis, release, or activity of GABA. Activity can be enhanced, for example, by enhancing the interaction between GABA and a cognate receptor. There are various ways to enhance this interaction, including increasing the concentration of GABA, blocking its reuptake, providing a receptor agonist, or altering the kinetics of receptor binding and signal transduction. GABA concentration can, in turn, be increased by increasing GABA synthesis or inhibiting GABA metabolism. GABA concentrations are, in effect, also increased by the administration of agents that mimic GABA. With respect to indirect stimulation, any agent (e.g., an antidepressant) that preferentially increases dopaminergic or noradrenergic activity in the prefrontal cortex can indirectly affect (i.e., stimulate) GABA in the prefrontal cortex. Mirtazapine is an example of an antidepressant agent that could be used to indirectly stimulate GABA; atomoxetine is an example of another type of agent that can be similarly used. Gabapentin (Neurontin™) is an example of an agent that mimics the effect of GABA, and direct stimulators include any benzodiazepine (e.g., oxazepam ((Serax®) or chlordiazepoxide), diazepam (Valium®) or alprazolam (Xanax®)). Other useful agents such as muscimol and baclofen may stimulate GABA through the GABAA or GABAB receptor, respectively. Other GABA agonists, analogues, or mimics include progabide, pregabalin, riluzole, vigabatrin, valproic acid (Depakote™), tiagabine (Gabitril™), lamotrigine (Lamictal™), phenytoin (Dilantin™), carbamazepine (Tegretol™) and topiramate (Topamax™). Other GABA agonists and compounds useful in targeting the prefrontal cortex include barbiturates, carisoprodol, chloral hydrate, glutethimide, L-theanine, kava, methaqualone, neuroactive steroids, z-drugs, propofol, scullcap, valerian, gamma-butyrolactone, gamma-hydroxybutyric acid, phenibut, deramciclane, hyperforin, gabaculine, phenelzine, valproate, vigabatrin, lemon balm (*Melissa offi-*

*cinalis*). One can also incorporate GABA per se, L-glutamine, picamilon, or tetanospasmin.

Benzodiazepine receptor expression can be assessed using methods known in the art. For example, receptors can be labeled with [$^3$H]PK11195 (see Javaid et al., *Biol. Psychiatry* 36:44-50, 1994; see also Chesley et al., *J. Clin. Psychiatry* 51:404-406, 1990). The data described below further suggests that benzodiazepines mediate certain aspects of cocaine reinforcement in rats.

In a fifth aspect, the invention features compositions (e.g., pharmaceutical compositions) that include a first agent that targets the HPA axis and a second agent that targets the sympathetic nervous system. Moreover, the compositions can be formulated such that they do not significantly lower plasma cortisol levels. Regardless of whether or not plasma cortisol levels are affected, the first and/or second agent(s) can be conjugated to a protein or other moiety that facilitates transport across the blood-brain barrier. The first agent that targets the HPA axis can be any of those described herein (for example, metyrapol, any of the agents described above in the context of the third aspect of the invention, or any of the nucleic acids or antibodies described in more detail below).

Agents that inhibit the sympathetic nervous system include those known in the art as "beta blockers." For example, the agent that inhibits activity in the sympathetic nervous system can be sotalol (Betapace®), imolol (Blocadren®), carteolol (Cartrol®), carvedilol (Coreg®), nadolol (Corgard®), nadol/bendroflunetazide (Corzide®), propranolol (Inderal®), propranolol/HCTZ (Inderide®), betaxolol (Kerlone®), penbutolol (Levatol®), metoprolol (Lopressor®), labetalol (Normodyne®), acebutolol (Sectral®), atenolol/HCTZ (Tenoretic®), atenolol (Tenormin®), timolol/HCTZ (Timolide®), metoprolol (Toprol®), labetalol (Trandate®), pindolol (Visken®), bisoprolol (Zebeta®), bisoprolol/HCTZ (Ziac®), esmolol (Brevibloc®), or combinations thereof.

In a sixth aspect, the invention features compositions (e.g., pharmaceutical compositions) that include a first agent that targets the HPA axis, a second agent that targets the prefrontal cortex, and a third agent that targets the sympathetic nervous system. Moreover, the compositions can be formulated such that they do not significantly lower plasma cortisol levels. Regardless of whether or not plasma cortisol levels are affected, the first and/or second agent(s) can be conjugated to a protein or other moiety that facilitates transport across the blood-brain barrier. The first, second, and third agents can be any of those described herein for targeting the HPA axis, the prefrontal cortex, and the sympathetic nervous system, respectively. For example, the first agent can be metyrapol, any of the agents described above in the context of the third aspect of the invention, or any of the nucleic acids or antibodies described in more detail below.

Generally, compounds incorporated into the present pharmaceutical compositions can be incorporated as racemic mixtures (e.g., roughly equal parts of each isomer) or purified and included in either the D- or L-form. Further, chemical compounds can be modified to become more lipophilic (or more hydrophobic), and such modifications may allow the compounds to more readily cross the blood-brain barrier. The compounds can be conjugated to a lipoamino acid or triglyceride to allow delivery into the brain via the respective transporter proteins for those compounds. The compounds (e.g., metyrapone, metyrapol, ketoconazole, and oxazepam) can also be conjugated to a ligand that binds a receptor that mediates the transport of substances into the brain. For example, an active can be conjugated to a ligand that binds a transferrin receptor or an insulin-like growth factor receptor. Alternatively, the compounds can be conjugated to antibodies that selectively bind such receptors. Further, these receptor binding proteins or antibodies can be attached to the surface of liposomes containing the compounds for delivery across the blood-brain barrier. In addition, cell penetrating peptides, such as the TAT peptide from HIV-1 can also be used as carriers to enhance the uptake of compounds that have been conjugated to it.

As noted, pharmaceutically active agents useful in the present compositions can be nucleic acids. These nucleic acids can serve as the first agent that targets the HPA axis by inhibiting, directly or indirectly, the expression of CRH, ACTH, or cortisol, or a receptor bound by one of these ligands (e.g., NR3C1). To directly inhibit the expression of CRH, ACTH, cortisol, or a receptor thereof, the nucleic acids can be antisense oligonucleotides or RNAs that mediate RNAi by specifically binding, due to sequence-specific complementarity, to a gene or mRNA encoding the ligand or receptor. To indirectly inhibit the expression of CRH, ACTH, or cortisol, or a receptor bound by one of these ligands, the nucleic acids can be antisense oligonucleotides or RNAs that mediate RNAi by specifically binding, due to sequence-specific complementarity, to a gene or mRNA encoding an enzyme or precursor in the synthetic pathway that produces the ligand, or a downstream effector activated by receptor binding. Similarly, nucleic acids can serve as the second agent that targets the prefrontal cortex by increasing GABA. For example, the nucleic acids can enhance the amount of L-glutamic acid decarboxylase, which catalyzes the reaction generating GABA from glutamate.

Nucleic acids having about 9-10 nucleotides or more (e.g., 12-14, 15-17, 18-20, 21-23, or 24-27 nucleotides; siRNAs generally have 21 nucleotides) are typically used to inhibit target expression, and nucleic acids of these lengths can be included in the present compositions. Regardless of length, the nucleic acids can be double-stranded or single-stranded and can include or constitute a sense or coding strand where transcription is desired, or an antisense or non-coding strand where the aim is to inhibit the expression of a target (e.g., CRH or ACTH). The nucleic acids can be synthesized using standard nucleotides or nucleotide analogs or derivatives (e.g., inosine, phosphorothioate, or acridine substituted nucleotides), which can alter base pairing with complementary sequences or provide increased resistance to nucleases. The stability or solubility of a given nucleic acid can be modified if desired by modifying the base moiety, sugar moiety, or phosphate backbone (e.g., as taught by Toulmé (*Nature Biotech.* 19:17, 2001) or Faria et al. (*Nature Biotech.* 19:40-44, 2001)). The deoxyribose phosphate backbone of nucleic acids can be modified to generate peptide nucleic acids (PNAs; see Hyrup et al., *Bioorganic & Medicinal Chemistry* 4:5-23, 1996), which are nucleic acid "mimics" in which a molecule's natural backbone is replaced by a pseudopeptide backbone and only the four nucleotide bases are retained. This allows specific hybridization to DNA and RNA under conditions of low ionic strength. PNAs can be synthesized using standard solid phase peptide synthesis protocols as described, for example by Hyrup et al. (supra) and Perry-O'Keefe et al. (*Proc. Natl. Acad. Sci. USA* 93:14670-675).

To inhibit expression, the nucleic acids can specifically bind either within the coding region of a targeted sequence or to a noncoding region (e.g., the 5' or 3' untranslated region). For example, a useful antisense oligonucleotide can be complementary to the region surrounding the translation start site of a targeted mRNA (e.g., between the −10 and +10 regions of a target gene of interest) or to a region in or around the polyadenylation signal. Gene expression can also be inhibited by targeting regulatory regions (e.g., promoters and/ or enhancers) to form triple helical structures that prevent transcription of the targeted gene (see generally, Helene, *Anticancer Drug Des.* 6:569-84, 1991; Helene, *Ann. N.Y. Acad. Sci.* 660:27-36, 1992; and Maher, *Bioassays* 14:807-15, 1992). The nucleic acids can also be so-called "switchback" nucleic acids, which are synthesized in an alternating 5'-3', 3'-5' manner, such that they base pair with first one strand of a duplex and then the other, eliminating the necessity for sizeable stretches of purines or pyrimidines on one strand of a duplex.

In other embodiments, the antisense nucleic acids can be anomeric nucleic acids, which form specific double-stranded hybrids with complementary RNA in which, contrary to the usual b-units, the strands run parallel to each other (Gaultier et al., *Nucleic Acids Res.* 15:6625-6641, 1987; see also Tanaka et al., *Nucl. Acids Res.* 22:3069-3074, 1994). Alternatively, antisense nucleic acids can comprise a 2'-o-methylribonucleotide (Inoue et al., *Nucleic Acids Res.* 15:6131-6148, 1987) or a chimeric RNA-DNA analogue (Inoue et al., *FEBS Lett.* 215:327-330, 1987).

We may refer to the nucleic acids as "isolated" when they are no longer associated with some or all of the flanking nucleic acid sequences with which they were naturally associated in vivo, and we may refer to the nucleic acids as "purified" when separated from some amount of the cellular material with which they were associated in vivo. For example, a nucleic acid sequence useful as a therapeutic agent as described herein can be at least 50% pure (e.g., at least or about 60%, 70%, 75%, 80%, 85%, 90%, 95%, 98%, or 99% of the composition can be the nucleic acid). The nucleic acids can of course be synthesized (rather than isolated or purified), and methods of generating nucleic acid constructs and delivering them to target cells are well known in the art. For example, the nucleic acids can be incorporated into a vector (e.g., an autonomously replicating plasmid or virus) prior to administration to a patient, and such vectors are within the scope of the present invention. The invention also encompasses genetic constructs (e.g., plasmids, cosmids, and other vectors that transport nucleic acids) that include a nucleic acid of the invention in a sense or antisense orientation. The nucleic acids can be operably linked to a regulatory sequence (e.g., a promoter, enhancer, or other expression control sequence, such as a polyadenylation signal) that facilitates expression of the nucleic acid. The vector can replicate autonomously or integrate into a host genome, and can be a viral vector, such as a replication defective retrovirus, an adenovirus, or an adeno-associated virus (e.g., the adeno-associated virus described in U.S. Pat. No. 7,955,595).

In addition, when present, regulatory sequences can direct constitutive or tissue-specific expression of the nucleic acid (e.g., expression in the skin or brain). Suitable neuronal specific promoters include, but are not limited to, neuron specific enolase (NSE) (Olivia et al., *Genomics* 10:157-165, 1991; GenBank Accession No: X51956), and human neurofilament light chain promoter (NEFL) (Rogaev et al., *Hum. Mol. Genet.* 1:781, 1992; GenBank Accession No: L04147). Glial specific promoters include, but are not limited to, glial fibrillary acidic protein (GFAP) promoter (Morii et al., *Biochem. Biophys Res. Commun.* 175:185-191, 1991; GenBank Accession No: M65210), S100 promoter (Morii et al., *Biochem. Biophys Res. Commun.* 175:185-191, 1991; GenBank Accession No: M65210) and glutamine synthase promoter (Van den et al., *Biochem. Biophys. Acta.* 2:249-251, 1991; GenBank Accession No: X59834). For expression in the hypothalamus, the nucleic acid constructs can include the CRH promoter, and for expression in the anterior pituitary, the nucleic acid constructs can include the ACTH promoter. Any portion of the respective promoters can be used so long as the portion is sufficient to direct tissue-specific expression.

Instead of generating nucleic acids that are expressed in particular tissues, the nucleic acids, including antisense nucleic acids, can be modified to target selected cells within the HPA axis, the prefrontal cortex and/or the sympathetic nervous system. For example, antisense nucleic acids can be linked to antibodies or other proteins (e.g., receptor ligands) that will specifically bind to cell surface receptors or other components associated with the target cell type. Similarly, the nucleic acids can include agents that facilitate their transport across the cell membrane (see, e.g., Letsinger et al., *Proc. Natl. Acad. Sci. USA* 86:6553-6556, 1989; Lemaitre et al., *Proc. Natl. Acad. Sci. USA* 84:648-652, 1987; and WO 88/09810) or the blood-brain barrier (see, e.g., WO 89/10134). In addition, nucleic acids can be modified with intercalating agents (Zon, *Pharm. Res.* 5:539-549, 1988). Antisense nucleic acids can also be delivered to cells using the vectors described herein. To achieve sufficient intracellular concentrations of antisense nucleic acids, one can express them in vectors having a strong promoter (e.g., a strong pol II or pol III promoter).

As described herein, antibodies can also be incorporated as pharmaceutically active agents in the present compositions, and the invention includes nucleic acids encoding those antibodies. These nucleic acids are useful in at least two ways; they can be used to produce antibodies in an expression system (from which the antibodies are harvested and prepared for administration in one or more of the compositions described herein) or they can be formulated and administered to a patient directly, in whom the antibodies will be subsequently produced.

We use the term "antibody" to broadly refer to proteins encoded by immunoglobulin genes that selectively bind a target of interest (e.g., CRH, ACTH, a CRH receptor, an ACTH receptor, or a GABA receptor) as well as to target-binding fragments and other variants thereof (e.g., a single-chain antibody, a humanized antibody, or an Fab fragment). Thus, the present compositions can include tetrameric antibodies of the immunoglobulin G class (IgG), and IgM, IgD, IgA, and IgE antibodies can also be used. The target- or antigen-binding fragment can be: (i) a Fab fragment (i.e., a monovalent fragment consisting of the VL, VH, CL and CH1 domains); (ii) a F(ab')$_2$ fragment (i.e., a bivalent fragment containing two Fab fragments linked by a disulfide bond at the hinge region); (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; or (vi) an isolated CDR. While the precise structure of the antibody can vary, what is required is that the antibody specifically bind a target described herein and alter that target—whether by enhancing or inhibiting its activity in keeping with the invention—in a way that confers a clinical benefit on a patient to whom the antibody is administered. For example, an antibody can specifically bind CRH or ACTH and inhibit their activity/function.

The antibodies can be polyclonal or monoclonal antibodies; may be chimeric, humanized, CDR-grafted, or human; and bi-specific antibodies that traverse the blood-brain barrier may be especially useful in targeting the brain. Generally, methods of producing antibodies are well known in the art. For example, human monoclonal antibodies can be generated in transgenic mice carrying human immunoglobulin genes rather than those of the mouse. Splenocytes obtained from these mice (after immunization with an antigen of interest) can be used to produce hybridomas that secrete human mAbs with specific affinities for epitopes from a human protein (see, e.g., WO 91/00906, WO 91/10741; WO 92/03918; WO 92/03917; Lonberg et al., *Nature* 368:856-859, 1994; Green et al., *Nature Genet.* 7:13-21, 1994; Morrison et al. *Proc. Natl. Acad. Sci. USA* 81:6851-6855, 1994; Bruggeman et al., *Immunol.* 7:33-40, 1993; Tuaillon et al., *Proc. Natl. Acad. Sci. USA* 90:3720-3724, 1993; and Bruggeman et al., *Eur. J. Immunol* 21:1323-1326, 1991). See also European Patent Application Nos. 125,023; 184,187; 171,496; and 173,494; see also WO 86/01533; U.S. Pat. No. 4,816,567; Better et al., *Science* 240:1041-1043, 1988; Liu et al., *Proc. Natl. Acad. Sci. USA* 84:3439-3443, 1987; Liu et al., *J. Immunol.* 139:3521-3526, 1987; Sun et al., *Proc. Natl. Acad. Sci. USA* 84:214-218, 1987; Nishimura et al., *Cancer Res.* 47:999-1005, 1987; Wood et al., *Nature* 314:446-449, 1985; Shaw et al., *J. Natl. Cancer Inst.* 80:1553-1559, 1988; Morrison et al., *Proc. Natl. Acad. Sci. USA* 81:6851, 1984; Neuberger et al., *Nature* 312:604, 1984; and Takeda et al., *Nature* 314:452, 1984).

For bi-specific antibodies, a first portion of the antibody can specifically bind a target as described herein (e.g., CRH, ACTH, a CRH receptor, an ACTH receptor, or a GABA receptor) and a second portion of the antibody can specifically bind a protein expressed at the blood-brain barrier, such as the transferrin receptor, which activates a molecular channel that normally imports iron into the brain. After binding the protein (e.g., the transferrin receptor), the antibody is transported into the brain, where it can act against, for example, CRH, ACTH, a CRH receptor, an ACTH receptor, or a GABA receptor. The affinity of the antibody for the first target can be higher than the affinity of the antibody for the second target (the blood-brain barrier-specific target such as the transferrin receptor) and the affinity of the antibody for the second target is preferably low enough that the antibody releases from the vasculature after crossing the blood-brain barrier. In one embodiment, the portion of the antibody that binds the transferrin receptor can be the same as or substantially similar to the transferrin receptor-binding portion of the antibody described by Yu et al. (*Science Trans. Med.* Vol. 3, Issue 84, 84ra44, 2011).

Human synthetic antibody libraries can be used for selection if desired and sorted against a target of interest (e.g., a CRH or ACTH receptor or a protein expressed at the blood-brain barrier). Positive clones can be identified by ELISA and DNA sequencing, and antibodies can be reformatted as necessary to full-length IgGs. Affinity maturation can be performed with combinatorial CDR mutagenesis. The antibodies can then be screened in vitro for their ability to inhibit the activity or function of their target (e.g., a CRH or ACTH receptor) and their affinity can be assessed by standard binding assays (e.g., a competition ELISA). Affinities can be varied by alanine substitution in, for example, one or more of the CDRs. Individual half-antibodies can be purified and combined, and bispecific antibodies can be purified by conventional means.

Expression vectors can be used to produce the proteins of the invention, including antibodies, ex vivo (e.g., the proteins of the invention can be purified from expression systems such as those described herein) or in vivo (in, for example, whole organisms).

The active pharmaceutical agents described herein can be variously formulated for administration to patients; a pharmaceutical composition including one or more agents that target the HPA axis, the prefrontal cortex and/or the sympathetic nervous system can be administered to a patient at therapeutically effective doses to reduce the risk or severity of addiction and the other conditions described herein. A therapeutically effective dose refers to an amount of the agent or combination of agents sufficient to improve at least one of the signs or symptoms of the addiction or of the other conditions described herein. The compositions can contain first and second agents by virtue of a physical combination of the agents per se, or the agents can be combined by virtue of a shared packaging (e.g., tablets containing a first active agent and tablets containing a second active agent can be combined in a single dispenser, such as a blister pack or similar dispensing device, optionally marked to indicate days of the week or times of the day at which the compositions should be administered). The pack or dispenser can, for example, comprise metal or plastic foil and can be accompanied by instructions for administration. Compositions packaged in this way may be referred to as "kits" or a "dual-packaged formulation" with instructions for their use. The therapeutic agents can also be combined within a single formulation (e.g., a tablet or capsule).

Many of the agents useful in the context of the present invention have been used previously to treat patients for other reasons. Where dosing information is available, it can be used to help determine effective doses of the agents in the presently described compositions. The dose used to treat a patient for addiction or another indication described herein can be the same as the dose that has been used to treat patients previously. The doses may also differ from previously prescribed dosages. For example, the effective dosages required in connection with the combination therapies described herein may be less than those previously proven safe and effective.

Toxicity and therapeutic efficacy can be determined, as necessary, by standard pharmaceutical procedures in cell cultures or experimental animals. For example, laboratory animals such as rodents and non-human primates can be used to determine the $LD_{50}$ (the dose lethal to 50% of the population) and the $ED_{50}$ (the dose therapeutically effective in 50% of the population). The dose ratio between toxic and therapeutic effects is the therapeutic index, which can be expressed as the ratio $LD_{50}:ED_{50}$. Compounds that exhibit large therapeutic indices are typically preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays (e.g., assays designed to determine whether a nucleic acid, nucleic acid-based agent, or a protein such as an antibody inhibits (or stimulates) the expression or activity of the ligand or receptor it is intended to inhibit (or stimulate)).

A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses (e.g., therapeutically effective doses) in humans. Levels in plasma can be measured, for example, by high performance liquid chromatography.

One of the greatest concerns in the treatment of drug addiction is the high rate of recidivism. This phenomenon can be tested in animals during reinstatement, which is a widely regarded preclinical model of the propensity to relapse to drug taking, and animal models of reinstatement can be used to further determine and define effective doses of the agents described herein. For example, animals can be taught to self-administer a drug until stable drug intake is maintained and then subjected to prolonged periods of extinction training or abstinence. Once the criteria for extinction are met, or following a specified period of abstinence, the ability of specific stimuli to reinstate responding on the manipulandum previously associated with the delivery of drug infusions is taken as a measure of drug seeking. This reinstatement of drug-seeking behavior can be elicited by priming injections of the drug itself in rats and monkeys (Stewart, *J. Psychiatr Neurosci.* 25:125-136, 2000) or by exposure to brief periods of intermittent electric footshock in rats (Shaham et al., *Brain Res. Rev.* 33:13-33, 2000; Stewart, *J. Psychiatr. Neurosci.* 25:125-136, 2000). Acute re-exposure to the self-administered drug (de Wit, *Exp. Clin. Psychopharmacol.* 4:5-10, 1996) and exposure to stress (Shiffman and Wills, *Coping and Substance Abuse*, Academic Press, Orlando, 1985; Lamon and Alonzo, *Addict. Behav.* 22:195-205, 1997; Brady and Sonne, *Alc. Res. Health* 23:263-271, 1999; Sinha, *Psychopharmacol.* 158:343-359, 2001; and Sinha et al., *Psychopharmacol.* 142:343-351, 1999), or simply the presentation of stress-related imagery (Sinha et al., *Psychopharmacol.* 158:343-359, 2000), have also been identified as potent events for provoking relapse to drug seeking in humans.

We initially found a dose of each of metyrapone and oxazepam that reduced cocaine self-administration without producing nonspecific debilitating effects on other behaviors. We then reduced the dose by one-half until we found a dose of each drug that no longer affected cocaine self-administration or any other observable behaviors (i.e., an ineffective dose). When we then combined the ineffective doses of the two drugs, cocaine self-administration was reduced. This suggests that although the two drugs produce their effects through different mechanisms, the effects are additive. Thus, we concluded that combining drugs that affect the HPA axis through different mechanisms can produce an additive effect on cocaine reward. Furthermore, by combining these drugs at concentrations that have no effect when the drugs are administered alone, we can minimize the potential toxic side effects (e.g., excessive decreases in plasma cortisol with metyrapone and the abuse liability of benzodiazepines) that may be associated with these compounds. Accordingly, the compositions of the present invention may include combinations of therapeutic agents, one or both of which are present at a dosage level lower than that which would be required to achieve an effect had the agent been administered alone; the dosages may be additive.

The dosage of at least one of the agents in the present compositions may be less than the dosage at which that agent is currently and typically prescribed. For example, where the present compositions include a benzodiazepine that is currently used in the treatment of anxiety, the amount of that compound administered to a patient for the treatment of addiction, another psychiatric disorder that may or may not be related to addiction, or a neurodegenerative disease can be less than a physician would have typically prescribed for the treatment of anxiety. In some instances, the dosages of both of the agents within the present compositions will be less than the traditional dosages of those agents.

The amounts of chemical compounds within the present compositions can vary. For example, a patient may receive from about 1-1000 mg of a given first agent and 1-1000 mg of a given second agent at defined intervals. For example, the patient can be treated every so-many hours (e.g., about every 2, 4, 6, 8, 12, or 24 hours), every so-many days (e.g., once a day, once every other day, once every three days), or every so-many weeks (e.g., once a week). For example, a patient may receive about or up to about 5-500 mg (e.g., about 5, 10, 15, 20, 25, 35, 45, 50, 100, 200, 250, 300, 400, 450, or 500) of a first agent and about or up to about 5-500 mg (e.g., 5, 10, 25, 35, 45, 50, 100, 200, 250, 300, 400, 450, or 500) of a second agent from 1-4 times per day. The amounts of the agents may be the same or different (e.g., the ratio of the first agent to the second can be about 1:1, 1.5:1; 2:1; 2.5:1, 4:1, 5:1, 10:1, 15:1, 20:1, 25:1, or 50:1). For example, a composition can contain the same amount of metyrapone and oxazepam; of metyrapol and oxazepam; of ketoconazole and alprazolam; of ketoconazole and oxazepam; of metyrapone and alprazolam; of metyrapol and alprazolam; of muscimol and CP-154,526; or of muscimol and metyrapone. Alternatively, these and other combinations of agents described herein may differ in amount or may differ at each administration in the manner described above. For example, a composition can include about 250 mg of metyrapone and about 5 mg of oxazepam, and a patient can be given, or may be instructed to take, these amounts one to four times daily. Other formulations are contemplated. For example, a composition can include 100-250 mg of metyrapone or metyrapol and 5-60 (e.g., 10) mg of oxazepam, and a patient may be given, or instructed to take, these amounts one to four times daily (e.g., about once a day to once every six hours). Dosages may also be expressed in terms of an amount administered according to the patient's weight. Thus, a first agent can be administered at, for example, about 5-20 mg/kg, and a second agent can be administered at, for example, about 0.1-0.5 mg/kg.

Pharmaceutical compositions for use in accordance with the present invention can be formulated in any conventional manner using one or more physiologically acceptable carriers or excipients. Thus, the agents, including compounds and their physiologically acceptable salts and solvates, whether administered as such or conjugated as described herein to facilitate transport across the blood-brain barrier, can be formulated for administration by or oral or parenteral administration (e.g., topical administration). Where the pharmaceutical compositions are formulated for topical administration, they may be formulated for administration to the skin or another accessible bodily tissue. For example, the compositions can be formulated to dissolve under or on the tongue or formulated for inhalation (e.g., as an aerosol).

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can also include polyethylene glycol, glycerin, and/or gelatin. The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Whether formulated for oral or parenteral (e.g., topical) administration, the compositions of the invention can be suitably formulated to give controlled release of the active agent(s).

The agents, including compounds (e.g., small organic molecules), nucleic acids, and protein-based actives such as antibodies, and conjugates and combinations thereof can be formulated for parenteral administration by injection (e.g., by bolus injection or continuous infusion, including infusion from an implanted device). Formulations for injection can be presented in unit dosage form (e.g., in ampoules or in multi-dose containers) with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle (e.g., sterile pyrogen-free water) before use.

As noted, the agents can also be formulated as a depot preparation. Such long acting formulations can be administered by implantation (for example, subcutaneously or intramuscularly) or by intramuscular injection. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

Formulations for direct delivery to the brain are also within the scope of the present invention. Thus, the compositions described herein can be formulated as sterile solutions for intracerebral, intraventricular or intrathecal injections or for infusion to the brain from a drug pump. While there are obviously risks and inconveniences with this route of administration, a patient may, in consultation with their physician, elect to be treated in this way if, for example, their symptoms are severe, alternatives are few (or exhausted) and the likelihood of success is enhanced by direct administration to the brain.

The compositions can also include an efflux inhibitor to help retain compounds in the vicinity of the brain. Some compounds that enter the brain fail to reach therapeutic levels and may be transported out of the brain via ABC efflux transport mechanisms, with P-glycoprotein (Pgp) being the principle efflux pathway at the blood-brain barrier. Thus, inclusion or co-administration of an inhibitor of Pgp or another transporter can enhance drug accumulation in the brain. The integrity of the blood-brain barrier can also be transiently manipulated to facilitate passage of the agents described herein from the systemic circulation into the brain. For example, the compositions can include mannitol or bradykinin, or these substances can be administered (e.g., by intra-arterial administration) separately as a part of the treatment regime. The blood-brain barrier can also be transiently opened using focused ultrasound to locally disrupt the barrier.

Various compositions described herein can be used to treat addiction to a variety of substances, including food when eating is excessive, or activities; to treat other conditions or disorders (e.g., psychological conditions such as depression, anxiety, and post-traumatic stress disorder), which may or may not be causally or otherwise related to addiction; to treat severe symptoms associated with menopause or the menstrual cycle; and to treat neurodegenerative disease. Thus, the invention features methods of treating patients and use of the compositions described herein in treatment or in the preparation of a medicament for treating the conditions described herein. Although we may refer to particular diseases and disorders (e.g., post-traumatic stress disorder), we use the term "disorder" broadly to refer to any of the conditions described herein (e.g., addiction) that are amenable to treatment.

The compositions described herein can be used to treat patients suffering from a disorder associated with aberrant activity in the HPA axis, the prefrontal cortex or, more generally, patients suffering from a disorder that affects brain function, particularly disorders related to stress or associated with the body's production of stress-induced substances such as cortisol. Thus, in a seventh aspect, the invention features methods of treating a patient suffering from addiction, which may be an addiction to a substance or an activity. The substance can be a chemical substance and can also be food in the event the patient consumes food in an uncontrolled, excessive manner. The patient may have, or be diagnosed as having, an addiction to a substance such as alcohol/ethanol, a chemical stimulant, a prescription (or prescribed) pain reliever, or a naturally-occurring plant-derived drug (e.g., a substance in marijuana or tobacco, such as nicotine). The chemical stimulant can be cocaine, an amphetamine, methamphetamine, crystalline methylamphetamine hydrochloride, methylphenidate, or a related stimulant. Where analogs of specific drugs are addictive, addictions to those analogs can also be treated. The drug can also be a barbiturate (e.g., thiamyl (Surital®), thiopental (Pentothal®), amobarbital (Amyta®), pentobarbital (Nembutal®), secobarbital (Seconal®), Tuinal (an amobarbital/secobarbital combination product), butalbital (Fiorina®), butabarbital (Butisol®), talbutal (Lotusate®), aprobarbital (Alurate®), phenobarbital (Luminal®), and mephobarbital (Mebaral®)) or opiate (e.g., heroin, codeine, hydrocodone, and related opioid drugs). Many prescription medications are subject to abuse, and patients addicted to such medications (e.g., medications prescribed for pain management such as percodan or percocet) can be treated as described herein. As noted, the substance in question may also be food where a patient relates to food in an addictive manner. Such patients may suffer from related conditions such as bulemia or obesity. Patients being treated with methadone are also candidates for treatment with the compositions described herein. The present compositions may help such patients step-down and discontinue use of methadone. Patients who engage in addictive behaviors can also be identified and treated. These patients may be suffering from an addiction to gambling or a sexual activity.

Addiction can be treated by administering to the patient an effective amount of a composition in which metyrapol is the sole active pharmaceutical agent (as characterized above as the first aspect of the invention). In that event, the patient may be suffering from an addiction to a substance other than cocaine. The compositions can be formulated and/or administered such that plasma cortisol levels are lowered, but the methods are not so limited. Formulations and administration regimes that do not lower plasma cortisol levels can also be employed. In treating addiction, one could administer, for example, a composition in which metyrapol is the sole active and has been conjugated to a protein or other moiety that facilitates transport across the blood-brain barrier (e.g., an antibody, such as an antibody that binds a receptor expressed in the vasculature of the blood-brain barrier). In other embodiments, addiction can be treated by administering to the patient an effective amount of a composition containing metyrapol as the first active pharmaceutical agent and one or more additional pharmaceutical actives that target the prefrontal cortex and/or the sympathetic nervous system (as characterized above as the second aspect of the invention). As the compositions including metyrapol and one or more additional active agents can be formulated such that they either lower or fail to lower plasma cortisol levels, methods of treating patients with those compositions would result in cortisol levels that are maintained in some instances and lowered in others. In other embodiments, addiction can be treated by administering to the patient an effective amount of a composition containing, as the sole active pharmaceutical agent, an agent that targets the HPA. As described above in describing the third aspect of the invention, these compositions can be formulated such that plasma cortisol levels are maintained in a patient to whom the composition is administered, and that outcome can be facilitated by conjugating the active to a protein or other moiety that facilitates its transport across the blood-brain barrier or increases its availability to tissues other than the adrenal gland. These compositions can also simply include an agent that facilitates transport across the blood-brain barrier or the retention of the active in the brain. In other embodiments, addiction can be treated by administering to the patient an effective amount of a composition containing a first agent that targets the HPA axis and a second agent that targets the prefrontal cortex. In accordance with the fourth aspect of the invention, these compositions can be formulated such that they do not significantly lower plasma cortisol levels and, whether plasma cortisol levels are affected or not, either or both of the first and second agents can be conjugated to a protein or other moiety that facilitates transport across the blood-brain barrier. These compositions can also simply include an agent that facilitates transport across the blood-brain barrier or improves the retention of the active in the brain. Other compositions usefully administered in the context of addiction are those described above as constituting the fifth and sixth aspects of the invention. Thus, one can administer an effective amount of a composition in which the first agent targets the HPA axis and the second agent targets the sympathetic nervous system or a composition containing a first agent that targets the HPA axis, a second agent that targets the prefrontal cortex, and a third agent that targets the sympathetic nervous system. As with other embodiments, the agent that targets the HPA axis or the agent that targets the prefrontal cortex can be conjugated to a protein or other moiety that facilitates transport across the blood-brain barrier. These compositions can also simply include an agent that facilitates transport across the blood-brain barrier or improves the retention of the active in the brain.

Any of the methods described herein for treating an addiction can include not only administration of the present compositions, but also psychotherapy or another form of psychological support to help the individual cope with the conditioned responses to environmental cues. Eventually, those cues will lose their saliency as they are no longer paired with the abused substance as abstinence is maintained, and pharmaceutical therapy may be lessened or discontinued over time.

In an eighth aspect, the present invention features methods of treating other disorders, including those considered to be psychiatric disorders, and including those that involve the HPA axis (or stress axis) and the prefrontal cortex. The disorders that can be treated include anxiety, including but not limited to anxiety associated with panic disorder, social anxiety disorder, generalized anxiety, and acute stress disorder. The disorder can also be an obsessive compulsive disorder (OCD) or post-traumatic stress disorder (PTSD), whether or not associated with anxiety. Patients diagnosed as suffering from depression can also be treated. Their depression can be, but is not necessarily, associated with major depressive disorder, dysthymia, bipolar depression, depression associated with medical conditions, and depression associated with substance abuse. Another disorder that can be treated is schizophrenia, and the patient may exhibit schizophrenia negative symptoms and/or cognitive impairment associated with schizophrenia. Also amenable to treatment are severe symptoms associated with menopause and premenstrual syndrome, including premenstrual dysphoric disorder.

The disorders described in the paragraph above can be treated by administering to the patient an effective amount of a composition in which metyrapol is the sole active pharmaceutical agent (as characterized above as the first aspect of the invention). The compositions can be formulated and/or administered such that plasma cortisol levels are lowered, but the methods are not so limited. Formulations and administration regimes that do not lower plasma cortisol levels can also be employed. In treating the disorders described immediately above (e.g., PTSD), one could administer, for example, a composition in which metyrapol is the sole active and has been conjugated to a protein or other moiety that facilitates transport across the blood-brain barrier (e.g., an antibody, such as an antibody that binds a receptor expressed in the vasculature of the blood-brain barrier). In other embodiments, the disorders described immediately above can be treated by administering to the patient an effective amount of a composition containing metyrapol as the first active pharmaceutical agent and one or more additional pharmaceutical actives that target the prefrontal cortex and/or the sympathetic nervous system (as characterized above as the second aspect of the invention). As the compositions including metyrapol and one or more additional active agents can be formulated such that they either lower or fail to lower plasma cortisol levels, methods of treating patients with those compositions would result in cortisol levels that are maintained in some instances and lowered in others. In other embodiments, the disorders described immediately above can be treated by administering to the patient an effective amount of a composition containing, as the sole active pharmaceutical agent, an agent that targets the HPA. As described above in describing the third aspect of the invention, these compositions can be formulated such that plasma cortisol levels are maintained in a patient to whom the composition is administered, and that outcome can be facilitated by conjugating the active to a protein or other moiety that facilitates its transport across the blood-brain barrier or increases its availability to tissues other than the adrenal gland. These compositions can also simply include an agent that facilitates transport across the blood-brain barrier or the retention of the active in the brain. In other embodiments, the disorders can be treated by administering to the patient an effective amount of a composition containing a first agent that targets the HPA axis and a second agent that targets the prefrontal cortex. In accordance with the fourth aspect of the invention, these compositions can be formulated such that they do not significantly lower plasma cortisol levels and, whether plasma cortisol levels are affected or not, either or both of the first and second agents can be conjugated to a protein or other moiety that facilitates transport across the blood-brain barrier. These compositions can also simply include an agent that facilitates transport across the blood-brain barrier or improves the retention of the active in the brain. Other compositions usefully administered in the context of addiction are those described above as constituting the fifth and sixth aspects of the invention. Thus, one can administer an effective amount of a composition in which the first agent targets the HPA axis and the second agent targets the sympathetic nervous system or a composition containing a first agent that targets the HPA axis, a second agent that targets the prefrontal cortex, and a third agent that targets the sympathetic nervous system. As with other embodiments, the agent that targets the HPA axis or the agent that targets the prefrontal cortex can be conjugated to a protein or other moiety that facilitates transport across the blood-brain barrier. These compositions can also simply include an agent that facilitates transport across the blood-brain barrier or improves the retention of the active in the brain.

In a ninth aspect, the invention features methods of treating neurodegenerative disease, including Alzheimer's disease, Parkinson's disease, Huntington's disease, and amyotrophic lateral sclerosis. These disorders can be treated by administering to the patient an effective amount of a composition in which metyrapol is the sole active pharmaceutical agent (as characterized above as the first aspect of the invention). The compositions can be formulated and/or administered such that plasma cortisol levels are lowered, but the methods are not so limited. Formulations and administration regimes that do not lower plasma cortisol levels can also be employed. In treating neurodegenerative disease, one could administer, for example, a composition in which metyrapol is the sole active and has been conjugated to a protein or other moiety that facilitates transport across the blood-brain barrier (e.g., an antibody, such as an antibody that binds a receptor expressed in the vasculature of the blood-brain barrier). In other embodiments, neurodegenerative disease can be treated by administering to the patient an effective amount of a composition containing metyrapol as the first active pharmaceutical agent and one or more additional pharmaceutical actives that target the prefrontal cortex and/or the sympathetic nervous system (as characterized above as the second aspect of the invention). As the compositions including metyrapol and one or more additional active agents can be formulated such that they either lower or fail to lower plasma cortisol levels, methods of treating patients with those compositions would result in cortisol levels that are maintained in some instances and lowered in others. In other embodiments, neurodegenerative disease can be treated by administering to the patient an effective amount of a composition containing, as the sole active pharmaceutical agent, an agent that targets the HPA. As described above in describing the third aspect of the invention, these compositions can be formulated such that plasma cortisol levels are maintained in a patient to whom the composition is administered, and that outcome can be facilitated by conjugating the active to a protein or other moiety that facilitates its transport across the blood-brain barrier or increases its availability to tissues other than the adrenal gland. These compositions can also simply include an agent that facilitates transport across the blood-brain barrier or the retention of the active in the brain. In other embodiments, addiction can be treated by administering to the patient an effective amount of a composition containing a first agent that targets the HPA axis and a second agent that targets the prefrontal cortex. In accordance with the fourth aspect of the invention, these compositions can be formulated such that they do not significantly lower plasma cortisol levels and, whether plasma cortisol levels are affected or not, either or both of the first and second agents can be conjugated to a protein or other moiety that facilitates transport across the blood-brain barrier. These compositions can also simply include an agent that facilitates transport across the blood-brain barrier or improves the retention of the active in the brain. Unlike the treatment of addiction or other psychiatric disorders, the present invention features methods of treating neurodegenerative disease with compositions including a first agent that targets the HPA axis and a second agent that targets the prefrontal cortex and neither the first nor the second agent may be conjugated to any other moiety. Further, compositions including the first and second agents may be free from any agent that affects transport across the blood-brain barrier or selectively directs the actives to any tissue other than the adrenal gland. Other compositions usefully administered in the context of neurodegenerative disease are those described above as constituting the fifth and sixth aspects of the invention. Thus, one can administer an effective amount of a composition in which the first agent targets the HPA axis and the second agent targets the sympathetic nervous system or a composition containing a first agent that targets the HPA axis, a second agent that targets the prefrontal cortex, and a third agent that targets the sympathetic nervous system. As with other embodiments, the agent that targets the HPA axis or the agent that targets the prefrontal cortex can be conjugated to a protein or other moiety that facilitates transport across the blood-brain barrier, and these compositions can also simply include an agent that facilitates transport across the blood-brain barrier or improves the retention of the active in the brain. The invention extends, however, in the treatment of neurodegenerative disease to administration of compositions including a first agent that targets the HPA axis and a second agent that targets the prefrontal cortex, neither of which may be conjugated to any other moiety. Further, compositions including the first and second agents may be free from any agent that affects transport across the blood-brain barrier or selectively directs the actives to any tissue other than the adrenal gland.

In a tenth aspect, the invention features methods of treating conditions that result in fluid retention, including fluid retention caused by kidney disease or malfunction, liver disease (e.g., cirrhosis), and congestive heart failure. These disorders can be treated by administering to the patient an effective amount of a composition in which metyrapol is the sole active pharmaceutical agent (as characterized above as the first aspect of the invention). The compositions can be formulated and/or administered such that plasma cortisol levels are lowered, but the methods are not so limited. Formulations and administration regimes that do not lower plasma cortisol levels can also be employed. In treating disorders that result in fluid retention, one could administer, for example, a composition in which metyrapol is the sole active and has been conjugated to a protein or other moiety that facilitates transport across the blood-brain barrier (e.g., an antibody, such as an antibody that binds a receptor expressed in the vasculature of the blood-brain barrier). In other embodiments, disorders that result in fluid retention can be treated by administering to the patient an effective amount of a composition containing metyrapol as the first active pharmaceutical agent and one or more additional pharmaceutical actives that target the prefrontal cortex and/or the sympathetic nervous system (as characterized above as the second aspect of the invention). As the compositions including metyrapol and one or more additional active agents can be formulated such that they either lower or fail to lower plasma cortisol levels, methods of treating patients with those compositions would result in cortisol levels that are maintained in some instances and lowered in others.

Any of the treatment methods described herein can include various steps, one of which can constitute identifying a patient in need of treatment. Physicians are well able to examine and diagnose patients suspected of suffering from addiction and/or another of the conditions described herein. Following a diagnosis, which may be made in the alternative, the physician can prescribe a therapeutically effective amount of a composition (e.g., a pharmaceutical composition comprising a first agent that targets the HPA axis and a second agent that targets the prefrontal cortex). While any mammal can be treated (e.g., a domesticated pet, such as a dog or cat), we expect the patient in most instances to be a human patient.

The success of the treatment can be assessed in a variety of ways, including objective measures (e.g., a reduction in the frequency or severity of drug self-administration or other addictive activity), a general improvement in health (e.g., an improvement in blood pressure, kidney function, liver function, or blood count) and/or subjective measures (e.g., a patient's report of reduced craving for a substance or activity or a better sense of well-being (e.g., reduced anxiety or an improved mood)).

EXAMPLES

Example 1

The Effects of Metyrapone and Oxazepam on Cocaine Self-Administration Following Adrenalectomy in Rats We have found that bilateral adrenalectomy (ADX), which essentially eliminates the production of corticosterone (CORT), abolishes the acquisition of intravenous cocaine self-administration (SA) without affecting food-maintained responding. This suppression of self-administration can be partially reversed by adding CORT to the rats' drinking water. Additionally, we have found that ADX reduces ongoing cocaine self-administration by approximately 25% but does not eliminate it, suggesting that CORT may be necessary for the acquisition, but not the maintenance of cocaine self-administration. In another experiment, pretreatment with metyrapone (MET), which blocks the synthesis of CORT, resulted in dose-related decreases in ongoing cocaine self-administration. Oxazepam (OX), a benzodiazepine, also dose-dependently decreased ongoing cocaine self-administration either when delivered alone or in combination with MET. The combination was effective at doses that produced no effects by themselves and had no effect on plasma CORT. The study described below was designed to determine if MET and OX would still decrease cocaine self-administration following ADX. If so, then mechanisms separate from the adrenal-based production of CORT must be responsible for their effects.

Subjects:

Male Wistar rats were housed in an AALAC-approved animal care facility and maintained at 85-90% of their free-feeding body weights. These rats were on a reversed 12-hour light, 12-hour dark cycle from the beginning of the experimental procedures.

Catheter Surgery:

A chronic indwelling jugular catheter (0.012 in i.d.×0.025 in o.d., silicone tubing) was implanted in each rat under pentobarbital anesthesia (50 mg/kg ip) with methyl atropine nitrate pretreatment (10 mg/kg ip). The animals were injected with sterile penicillin G procaine suspension (75,000 units, im) immediately before surgery and allowed 5-7 days to recover.

Adrenalectomy Surgery:

Animals were anesthetized with pentobarbital (50 mg/kg ip) with methyl atropine nitrate pretreatment (10 mg/kg ip). The adrenal glands were located through an incision and removed. The animals were injected with sterile penicillin G procaine suspension (75,000 units, im) and allowed to recover from surgery for 7 days. After ADX, the rats received drinking water containing 0.9% saline and 1.0% sucrose. Animals in the SHAM group received the same surgery except that the adrenal glands were not removed. They continued to receive tap water to drink.

Equipment:

Sound-attenuating operant conditioning chambers (Med-Associates, Inc.) were equipped with two response levers and a stimulus light located directly above each lever. A food pellet dispenser was located between the levers. Each chamber also had a motor driven syringe pump for drug delivery and a counterbalanced swivel apparatus to allow relatively free movement within the chamber. An IBM-compatible personal computer and interface system was used to program the procedure and collect the experimental data.

Alternating Schedule of Cocaine and Food Reinforcement:

Following recovery from catheter surgery, the rats were trained to respond under a multiple, alternating schedule of food reinforcement and cocaine self-administration. They were allowed access to either reinforcer for 15 minutes (a bin) at a time during the 2-hour behavioral session with a 1 minute timeout between each bin. Each individual reinforcer required the completion of 4 responses (FR4) to be delivered. Each food trial was followed by a 35-second timeout, and each infusion of cocaine (0.25 mg/kg/infusion) was delivered over 5.6 seconds followed by a 20-second timeout. Food-maintained responding was used as a control for the potential non-specific effects of the drugs and the adrenalectomy. Saline substitution and food extinction probes were conducted at least every 2 weeks to demonstrate that the animals could differentiate between the presence or absence of cocaine. After responding for both reinforcers had stabilized at FR4, the animals were tested with Vehicle (VEH). MET 50, OX5, OX10, MET 50/OX 5, and MET 50/OX 10 (mg/kg). The animals were then adrenalectomized. After recovering for 1 week, they were again allowed access to cocaine and food reinforcement. After responding for both reinforcers had stabilized once again, the animals were again tested with the same doses of MET and OX.

Hormone Measurements:

Blood was collected via the implanted catheters at the end of the behavioral test sessions for the measurement of plasma CORT and adrenocorticotropin releasing hormone (ACTH). The samples were kept on ice until centrifuged in a refrigerated centrifuge and the plasma collected and frozen until assayed. Plasma CORT and ACTH (ng/ml) were subsequently determined by radioimmunoassay.

Results:

Metyrapone and oxazepam were as effective, and possibly even more effective, in blocking cocaine self-administration following adrenalectomy when compared to pre-adrenalectomy values. Adrenalectomy by itself reduced self-administration by 15% while the reduction from metyrapone and oxazepam doses and combinations reduced it by 16-74%. The effects on food self-administration were essentially unchanged by adrenalectomy although the combinations appeared to have more of an effect following adrenalectomy. Corticosterone was not changed by any of the doses of metyrapone or oxazepam before adrenalectomy and was virtually eliminated after adrenalectomy. ACTH was not changed by any of the doses of metyrapone or oxazepam before adrenalectomy but was very high after adrenalectomy due to the loss of the negative feedback from the adrenal glands.

We have concluded that the effects of metyrapone and oxazepam on cocaine self-administration are not dependent on plasma corticosterone. Rat appear even more sensitive to the effects of metyrapone and oxazepam after adrenalectomy. These data suggest that there must be a mechanism possibly independent of the HPA axis involved in the effects of these drugs on the maintenance of cocaine self-administration.

Example 2

Effects of the Combination of Metyrapone and Oxazepam on Methamphetamine Seeking in Rats We have previously reported that combining low doses of metyrapone (a corticosterone synthesis inhibitor) and oxazepam (a benzodiazepine receptor agonist) reduces intravenous cocaine self-administration and the cue-induced reinstatement of extinguished cocaine seeking in rats. This study was designed to investigate whether or not the combination of metyrapone and oxazepam would also block cue reactivity associated with methamphetamine self-administration in rats. Adult male rats were implanted with jugular catheters and trained to self-administer methamphetamine (0.06 mg/kg/infusion) during daily 2 hour sessions. During training, methamphetamine delivery was paired with the presentation of a tone and the illumination of a houselight. Once stable baselines of self-administration were observed, rats were placed into forced abstinence, where the rats remained in their home cages for 14 days. During cue reactivity testing on the 15$^{th}$ day, the rats were placed in the operant chambers and responding only resulted in the presentation of the conditioned reinforcer (i.e., the houselight and tone previously paired with methamphetamine self-administration); no methamphetamine was delivered. The response-contingent presentation of the conditioned reinforcer reliably maintained methamphetamine seeking (i.e., lever pressing) following vehicle pretreatment. Pretreatment with combinations of oxazepam (OX) and metyrapone (MET) (5 mg/kg oxazepam and 25 mg/kg metyrapone or 10 mg/kg oxazepam and 50 mg/kg metyrapone, ip) resulted in a dose-related attenuation of methamphetamine seeking. These data suggest that the combination of oxazepam and metyrapone is useful in blocking the ability of environmental cues to stimulate methamphetamine seeking.

Subjects:

Adult male Wistar rats (n=26) were maintained at 85 to 90% of their free-feeding body weights and allowed free access to water. Each rat was implanted with a chronic indwelling jugular catheter and allowed a minimum of five days to recover following surgery. The patency of the catheters was tested weekly.

Equipment:

Behavioral experiments were conducted in standard PLEXIGLAS® and stainless steel, sound-attenuated operant conditioning chambers (Med-Associates, Inc.). Each experimental chamber was equipped with two response levers mounted on one wall of the chamber, and a stimulus light was located above each lever. The chambers were also equipped with a house light and tone generator used to produce a "cue" that was paired with each methamphetamine infusion.

Self-Administration Training:

Rats were trained to self-administer methamphetamine by pressing one of the response levers (i.e., the "active" lever) under a fixed-ratio 4 (FR4) schedule of reinforcement during daily 2-hour sessions. At the start of each session, a stimulus light above the active lever was illuminated to indicate the availability of methamphetamine. Initially, one depression of the active lever (fixed-ratio 1 or FR1) resulted in an intravenous infusion of methamphetamine (0.06 mg/kg/infusion delivered in 200 µl 0.9% heparinized NaCl over 5.6 seconds) and the concurrent presentation of the house light and tone cues. Thus, the cues became a conditioned, or secondary, reinforcer. A 20 second timeout period (TO) followed each infusion. The stimulus light above the active lever was darkened during the infusion and timeout period and was illuminated again once the timeout ended. When responding on the active lever varied less than 20% for two consecutive days, the response ratio was changed from FR1 to FR2. When this behavioral criterion was again met, the response requirement was increased from FR2 to FR4. Stable baseline responding (less than 10% variation for 3 consecutive sessions) under the FR4 schedule of reinforcement was achieved after a minimum of 10 days. Responses on the inactive lever resulted in no programmed consequences at any time.

Abstinence:

Once the criteria for stable responding under the FR4 schedule was met, forced abstinence commenced. Immediately following the last self-administration session, the rat was placed in its home cage and remained there for 14 consecutive days with no access to methamphetamine or drug-paired cues.

Cue-Reactivity Testing:

On the 15$^{th}$ day, cue-reactivity testing was conducted. Rats were treated with either vehicle or one of two dose combinations of oxazepam and metyrapone (5 mg/kg oxazepam and 25 mg/kg metyrapone or 10 mg/kg oxazepam and 50 mg/kg metyrapone, ip) 30 minutes before the start of the test session. They were then placed into the experimental chambers and the active lever stimulus light was illuminated. Responses on both levers were recorded but responses on the inactive lever resulted in no programmed consequences. After a response on the active lever, the tone and house light conditioned cues were presented for 5.6 seconds and the stimulus light was darkened for 20 seconds (as during regular self-administration); however, no methamphetamine was infused. Each rat was tested up to 4 times in an alternating vehicle and 5 mg/kg oxazepam and 25 mg/kg metyrapone or vehicle and 10 mg/kg oxazepam and 50 mg/kg metyrapone schedule.

Blood Plasma Collection Assay:

Blood samples were drawn via the indwelling jugular catheter or tail-snip at three time points, immediately following the last session of stable FR4 self-administration responding, the last (14$^{th}$) day of forced abstinence, and immediately following the cue-reactivity testing session, to measure fluctuations in plasma corticosterone. Corticosterone samples were centrifuged and the plasma was collected and immediately frozen at −20° C. Plasma samples were analyzed via radio-immunoassay and read in a gamma counter.

Results:

Both combinations of oxazepam and metyrapone significantly reduced active lever responding. Plasma corticosterone was not significantly different between groups at all three time points. FR4 is last day of stable self-administration responding, ABST is last day of forced abstinence, and CUE-R is cue-reactivity testing day.

The number of responses on the active lever on cue-reactivity testing day was significant between vehicle and Ox5/Met 25 ($p<0.05$) and between vehicle and Ox10/Met50 ($p<0.001$) but was not significant between Ox5/Met25 and OX10/Met50 ($p>0.05$, 1 way ANOVA). Last day of stable FR4 responding plasma corticosterone was not significantly different between all groups ($p>0.05$). Last day of forced abstinence plasma corticosterone was not significantly different between all groups ($p>0.05$). Cue-reactivity testing day corticosterone was not significantly different between all groups ($p>0.05$).

Based on the results described above, we have concluded that pretreatment with combinations of oxazepam and metyrapone (5 mg/kg oxazepam and 25 mg/kg metyrapone or 10 mg/kg oxazepam and 50 mg/kg metyrapone, ip) resulted in a dose-related attenuation of methamphetamine seeking. Corticosterone levels were not significantly altered relative to vehicle at any of the time points through the experiment. These data suggest that the combination of oxazepam and metyrapone is useful in blocking the ability of environmental cues to stimulate methamphetamine seeking without altering plasma corticosterone.

Example 3

Effects of the Combination of Metyrapone and Oxazepam on Intravenous Nicotine Self-Administration in Rats The study described here was designed to test the effects of a combination of metyrapone and oxazepam on nicotine self-administration in rats. Several dose combinations of metyrapone (25 or 50 mg/kg) and oxazepam (5 or 10 mg/kg) were tested in rats trained to intravenously (IV) self-administer nicotine (0.03 mg/kg/infusion) during 1-hour self-administration sessions using both fixed-ratio and progressive-ratio schedules of reinforcement. The administration of low doses of metyrapone and oxazepam in combination decreased intravenous nicotine self-administration in rats under both schedules of reinforcement. Varenicline was also tested using the fixed-ratio schedule, and reductions in drug intake observed with varenicline were comparable to those seen with the lowest dose of the combination tested. The results of this study suggest the feasibility of the combination of metyrapone and oxazepam for smoking cessation in humans.

It has been reported that the α4β2 nicotinic acetylcholine receptor partial agonist varenicline (Keating and Lyseng-Williamson, *Pharmacoeconomics* 28(3):231-254, 2010) has increased efficacy for smoking cessation compared to either bupropion (Cahill et al., *Drug Safety* 32(2):119-135, 2009; Gonzales et al., *JAMA* 296(1):47-55, 2006; Jorenby et al., *JAMA* 296(1):56-63, 2006) or nicotine replacement therapy (Aubin et al., *Thorax* 63(8):717-724, 2008; Cahill et al., *Drug Safety* 32(2):119-135, 2009) although the quit rates after one year are only 14% (Nides et al., *Arch. Intern. Med.* 166(15):1561-1568, 2006). These data suggest that there is a continuing need for the development of safe and effective pharmacotherapies for the treatment of nicotine dependence.

Animals:

Wistar-derived male rats (250-300 g) were purchased from Harlan Laboratories (Livermore, Calif.), housed in groups of two, and maintained in a temperature-controlled environment on a 12 h:12 h light cycle. Before testing, animals were provided free access to food and water during a one-week habituation period, and were handled daily for several days to desensitize them to handling stress. Each rat included in the data analysis received all treatments in order to obtain reliable estimates of drug effects and decrease the impact of inter-animal variability. Animals were handled, housed, and sacrificed in accord with the current NIH guidelines and all applicable local, state, and federal regulations and guidelines.

Drug Treatments:

Rats received one of several dose combinations of metyrapone (25 or 50 mg/kg, Sigma Aldrich) and oxazepam (5 or 10 mg/kg, Sigma Aldrich) or vehicle administered intraperitoneally as a suspension containing 5% Alkamuls EL-620 (Rhodia) in 0.9% saline. Varenicline-HCl (Ontario Chemicals), at 1 mg/kg (expressed as free base), was used as a positive control and administered subcutaneously. Nicotine hydrogen tartrate (Sigma Aldrich) was dissolved in isotonic saline at 0.3 mg/mL (expressed as free base), adjusted to pH 7.0, and diluted to deliver 0.03 mg/kg/infusion. All test compounds were administered 30 minutes prior to nicotine self-administration sessions in a volume of 1 mL/kg. The doses tested in the fixed-ratio study were: 50 mg/kg metyrapone:10 mg/kg oxazepam; 50 mg/kg metyrapone:5 mg/kg oxazepam; 25 mg/kg metyrapone:5 mg/kg oxazepam; and 1 mg/kg varenicline. The lowest dose combination (i.e., 25 mg/kg metyrapone:5 mg/kg oxazepam) was tested in the progressive-ratio experiment. We selected these doses based on our previous data with this drug combination in a rat model of cocaine self-administration (Goeders and Guerin, *Pharmacol. Biochem. Behav.* 91(1):181-189, 2008).

Apparatus:

Food training and nicotine self-administration took place in 8 standard Coulbourn™ operant conditioning chambers. Each chamber was housed in a sound-attenuating chamber. Operant chambers were equipped with two levers mounted 2 cm above the floor and a cue light mounted 2 cm above the right lever (active lever) on the back wall of the chamber. For food training, a food hopper was located 2 cm to the left/right of either lever in the middle of the back wall. Intravenous infusions were delivered in a volume of 0.1 mL over a 1-sec interval via a motor-driven infusion pump (Razel) housed outside of the sound-attenuating chamber.

Food Training:

Lever pressing was established as demonstrated previously (Hyttia et al., *Psychopharmacology (Berl.)* 125(3):248-254, 1996). Initially, rats were restricted to 15 grams of food daily to maintain them at approximately 85% of their free-feeding body weights. After the second day of food restriction, rats were trained to respond under a fixed-ratio 1 (FR1) schedule of food reinforcement (i.e., 1 food pellet was delivered following each lever press) with a 1-second time-out (TO-1 s) following each pellet delivery, and the response requirement was gradually increased to a FR1, TO-20 s schedule of reinforcement. Training sessions were administered twice daily, and each session lasted for 30 minutes. Once rats obtained steady baseline responding at a FR1, TO-20 s schedule of reinforcement, defined as less than 20% variability across 3 consecutive sessions, they were returned to ad libitum feeding in preparation for surgical implantation of the intravenous jugular catheter.

Surgery:

Rats were anesthetized with an isoflurane-oxygen mixture (1-3% isoflurane) and a chronic silastic jugular catheter was inserted into the external jugular vein and passed subcutaneously to a polyethylene assembly mounted on the animal's back. The catheter assembly consisted of a 13-cm length of silastic tubing (inside diameter 0.31 mm; outside diameter 0.64 mm), attached to a guide cannula bent at a right angle. The cannula was embedded in a dental cement base and anchored with a 2×2 cm square of durable mesh. The catheter was passed subcutaneously from the rat's back to the jugular vein where it was inserted and secured with a non-absorbable silk suture. Upon successful completion of surgery, rats were given 5 days to recover before baseline self-administration sessions started. During the recovery period, rats remained on ad libitum food access and had their catheter lines flushed daily to prevent blood coagulation and infection.

Nicotine Self-Administration:

Following successful recovery from surgery, rats were again food deprived to 85% of their free-feeding body weights and were trained to self-administer nicotine (0.03 mg/kg/infusion, IV) during 1-hour baseline sessions conducted 5 days per week under a FR1, TO-20 s schedule of reinforcement until stable responding was achieved. Stable responding was now defined as less than 20% variability across 2 consecutive sessions. After stable responding for nicotine was achieved, the various dose combinations of metyrapone and oxazepam or vehicle were tested using a within-subjects Latin square design (LSD). After the testing of a dose, rats were allowed to reestablish stable baseline responding before the next dose was tested. Following the LSD dose testing with metyrapone and oxazepam, rats were run under baseline conditions for a minimum of 5 days until stable responding was achieved, after which the positive control varenicline (1 mg/kg, administered subcutaneously) was tested. Upon completion of varenicline testing, rats were again run under baseline conditions for a minimum of 5 days until stable responding was achieved. The same rats were then tested using a progressive-ratio (PR) schedule of reinforcement, with each nicotine infusion resulting in a progressive increase in the number of lever presses required to obtain the subsequent infusion. The progression of lever presses was as follows: 1, 2, 4, 6, 9, 12, 15, 20, 25, 32, 40, 50, 62, 77, 95, etc., derived from the formula ((5×e0.2n)−5) rounded to the nearest integer, where n is the position in the sequence of ratios. For PR testing, half of the rats were tested with metyrapone and oxazepam and the other half tested with vehicle on PR day 1. Following PR day 1, rats were again run under baseline conditions (FR1, TO-20) at 0.03 mg/kg/infusion until stable responding was again observed. A second PR session was then conducted with rats that received drug treatment in the first PR session receiving vehicle and rats that received vehicle in the first PR session receiving metyrapone and oxazepam. Catheters were flushed before and after each test session to ensure catheter patency, prevent blood coagulation, and reduce risk of infection. One rat was removed during the study due to catheter failure; the data shown represent the response of 8 rats that completed testing with all test agents.

Data Compilation, Processing, Analysis:

Data were collected on-line simultaneously from multiple operant chambers. Data from the LSD nicotine self-administration experiment were reported as the mean cumulative number of nicotine-reinforced responses. Results from the PR study were reported as the mean number of reinforced responses and the breakpoint. In general, tests for homogeneity of variance were first performed on the data. If the scores did not violate the assumption of homogeneity of variance, appropriate analyses of variance (ANOVA) were performed. Test data were analyzed using the StatView statistical package on a PC-compatible computer. For the analysis of all dose response curves, a repeated measures ANOVA was conducted. Follow-up analyses using paired t-tests were conducted where appropriate.

Results:

Under control conditions (vehicle treatment), rats received an average of 15.0±1.5 infusions of nicotine over the 1-hour test session under the FR1-TO-20 s schedule of reinforcement. Treatment with the combination of metyrapone:oxazepam reduced nicotine self-administration in a dose-related fashion, with dose ratios of 25:5 mg/kg, 50:5 mg/kg and 50:10 mg/kg reducing nicotine infusions to 7.1±1.6, 5.3±1.3 and 3.1±1.0, respectively.

An ANOVA of treatment groups revealed that the effect of metyrapone:oxazepam on nicotine intake relative to vehicle was significant $[F(3,21)=16.970, p<0.0001]$. Follow-up analysis (i.e., paired t-test) of individual dose combinations of metyrapone and oxazepam revealed that results for all dose combinations were significantly different from those obtained with vehicle (metyrapone:oxazepam, 25:5 mg/kg, p=0.0091; 50:5 mg/kg, p=0.008; 50:10 mg/kg, p=<0.0001). Analysis of order effects, using the average value of all rats within each treatment day, found no significant findings.

Varenicline treatment was found to reduce nicotine infusions from 15.4±1.0 to 7.7±1.2. An ANOVA of these data revealed that this reduction in the number of nicotine infusions during the 1-hour self-administration session was statistically significant $[F(1,7)=47.042, p<0.0003]$. A comparison of the varenicline results with those seen with metyrapone:oxazepam showed that at all doses tested, the metyrapone:oxazepam combination was more effective than varenicline at reducing nicotine self-administration.

The lowest dose combination of metyrapone:oxazepam (25:5 mg/kg) was tested under the progressive-ratio schedule. Pretreatment with metyrapone:oxazepam reduced the number of nicotine infusions from 6.1±0.5 to 2.8±0.6. The breakpoint was reduced from 12.6±1.6 lever presses with vehicle to 3.9±0.9 with metyrapone:oxazepam. An ANOVA of the progressive-ratio data revealed that pretreatment with 25:5 mg/kg metyrapone:oxazepam resulted in a significant decrease in the total number of nicotine infusions $[F(1,7)=15.997, p<0.0055]$ and the breakpoint $[F(1,7)=19.533, p<0.0035]$. Varenicline was not tested with the progressive-ratio schedule.

A number of embodiments of the invention have been described. Nevertheless, it will be understood that various modifications may be made without departing from the spirit and scope of the invention. Accordingly, other embodiments are within the scope of the following claims.

Example 4

Effects of the Combination of Metyrapone and Oxazepam on Cocaine Craving and Cocaine Taking: A Double-Blind, Randomized, Placebo-Controlled Pilot Study This study was designed to assess the safety and efficacy of combinations of the cortisol synthesis inhibitor metyrapone, and the benzodiazepine oxazepam, in 45 cocaine-dependent individuals. The subjects were randomized to a total daily dose of 500 mg metyrapone/20 mg oxazepam (low dose), a total daily dose of 1500 mg metyrapone/20 mg oxazepam (high dose), or placebo for six weeks of treatment. The outcome measures were a reduction in cocaine craving and associated cocaine use as determined by quantitative measurements of the cocaine metabolite BE in urine at all visits. Of the randomized subjects, 49% completed the study. The combination of metyrapone and oxazepam was well tolerated and tended to reduce cocaine craving and cocaine use, with significant reductions at several time points when controlling for baseline scores.

Our study (ClinicalTrials.gov: NCT00567814) evaluated whether the combination of metyrapone and oxazepam reduced cocaine craving and use in cocaine-dependent subjects in a community-based environment. This prospective, single center, randomized, placebo-controlled, double-blind study was conducted at the Psychopharmacology Research Unit at the Louisiana State University Health Sciences Center in Shreveport (LSUHSC-S). Subjects were randomized to a low total daily dose of 500 mg metyrapone/20 mg oxazepam, a high total daily dose of 1500 mg metyrapone/20 mg oxazepam, or placebo. The 6-week treatment period, with visits on Day 0 and Day 3 each week (Visits 1 through 12), was followed by an end-of-study visit on Week 7, Day 0 (Visit 13) and a follow-up visit 7 to 14 days after the end of treatment (Visit 14). Drug and placebo were supplied in two divided doses for twice daily administration.

We enrolled 45 subjects who met the Diagnostic and Statistical Manual of Mental Disorders (DSM-IV) criteria for cocaine dependency using the Mini-International Neuropsychiatric Interview (MINI Sheehan et al., *J. Clin. Psychiatry* 59

(Suppl. 201:22-33; quiz 34-57). Subjects were randomized to treatment groups based on the order in which they entered the study.

Subjects were men and women, 18 to 65 years old, who requested treatment for cocaine addiction, were able to provide written informed consent, and had a benzoylecgonine (BE)-positive urine test within the 14-day screening period. Exclusion criteria included any prominent DSM-IV axis I disorder other than cocaine dependence as determined by a psychiatrist at the initial interview, abuse of other psychoactive substances that did not meet the criteria for dependence, and alcohol dependence that did not require medical detoxification were acceptable as long as cocaine was the primary drug of choice. Other exclusion criteria included liver enzymes >2 times normal, serum cortisol <3 µg/dL at any time before or during the study, a history of hepatitis or disorders requiring chronic treatment with steroids at screening or in the past, a significantly abnormal ECG, pregnancy, or the use of any concomitant medication that would interfere with study medications (e.g., other benzodiazepines).

During the 6-week treatment period, subjects were instructed to take blinded capsules twice daily with food for a daily total of 500 mg metyrapone/20 mg oxazepam, 1500 mg metyrapone/20 mg oxazepam (which started with the low dose in Week 1 and escalated to the high dose for the remaining 5 weeks), or placebo (lactose). Psychosocial support was not provided, to avoid confounding effects and to attempt to isolate the effect of medication alone.

Cocaine craving was evaluated using two versions of the Cocaine Craving Questionnaire (CCQ), a subject-rated, self-administered questionnaire that asks subjects to rate their level of agreement with each item based on a 7-point Likert-type scale. CCQ items assess subjects' current status regarding their desire to use cocaine, anticipation of positive outcomes from use, anticipation of relief from withdrawal or negative mood symptoms, intent to use cocaine, and lack of control over use (Tiffany et al., *Drug Alcohol Depend.* 34:19-28, 1993). The CCQ-Now consists of 45 questions. The CCQ-Brief extracts 10 of the 45 questions from the CCQ-Now. The CCQ-Now was administered at Visit 1 and at the end-of-study Visit 13; the CCQ-Brief was administered at all other visits. There were no missing data in the CCQ-Brief. In a few instances for the CCQ-Now, the total score was obtained by imputing the average of available question responses at that visit for a subject rather than dropping the record from the analysis.

Cocaine use was determined by quantitative measurements of the cocaine metabolite benzoylecgonine (BE) in urine at all visits. Other efficacy measures assessed at all visits included concomitant drug use, which was measured by the urine drug screen (including cotinine levels in subjects who used nicotine products), and self-reported cocaine and alcohol use. The Hamilton Anxiety (HAM-A) and Hamilton Depression (HAM-D) Scales were conducted at Visits 1, 2, 3, 5, 7, 9, and 11, at the end-of-study Visit 13 and at the follow-up Visit 14.

The primary efficacy variable was the mean change in the CCQ-Brief from the first administration (Visit 2) to the last administration (Visit 12) in the Efficacy Evaluable data set for the high- and low-dose groups combined ("pooled group"), compared with placebo subjects with the last observation carried forward (LOCF). The primary efficacy analysis was based on a repeated measures model with factors for treatment, time, and time by treatment with baseline as a covariate. No adjustments for a multiplicity of endpoints were made due to the exploratory nature of the study. Efficacy analyses were also performed by comparing the individual treatment arms against the placebo arm using the model described above.

The primary analysis group for safety included all subjects who received at least one dose of study medication according to the randomization scheme. Adverse events were coded using Medical Dictionary for Regulatory Activities (MedDRA Version 10.0). The number and percent of subjects with a treatment-emergent event were summarized for each treatment arm. Summary statistics by treatment group (i.e., n, mean, standard deviation, median, minimum, and maximum) were calculated for continuous variables. Categorical variables (n and percentages) were summarized in tabular form. No inferential testing was planned other than ad-hoc testing for an event of clinical interest.

Two post-hoc analyses were performed to aid in interpreting the study results. First, the baseline characteristics of the Efficacy-Evaluable and Not Efficacy-Evaluable populations were analyzed to determine whether the high dropout rate resulted in a detectable skewing of the patient population. Second, a power analysis was performed using the observed placebo response in the change in CCQ-Brief and the size of the Efficacy Evaluable data set to determine whether it was statistically likely to achieve the prospectively defined primary endpoint.

Overall, 49% of randomized subjects completed the study. Most discontinuations (72%) were the result of subjects being lost to follow up. The loss of subjects due to adverse events is described in the Safety section below. Of the 45 subjects randomized, 26 were evaluable for efficacy. The Efficacy Evaluable data set included an approximately equal number of subjects in the low-dose, high-dose, and placebo groups (9, 8, and 9 respectively).

Cocaine craving was the primary prospectively-defined endpoint for this study. As subjects were randomized based on the order of entry into the study and not on the basis of any medical or scientific parameter, the possibility of differences among groups at baseline existed. During data analysis after study end, baseline levels of craving measured at Visit 1 by the CCQ-Now were found to be slightly higher in the placebo group (4.13) compared with the low-dose (3.55) and high-dose (3.55) groups. These craving levels were comparable to those in previous studies in similar populations based on the CCQ-Now results (Tiffany et al., *Drug Alcohol Depend.* 34:19-28, 1993). A difference between groups was again seen at Visit 2, when CCQ-Brief values were also higher in the placebo group (3.5) than in the low-dose (2.3) and high-dose (2.4) groups.

Although very rapid changes in craving were seen in the first weeks of the trial, these do not appear to be drug-related and are likely to represent a placebo effect of entry into treatment. While this effect might have been minimized by the use of a placebo run-in, this would have prolonged the trial and made subject retention even more difficult.

After Visit 6, there were trends favoring mean change from initial administration of the CCQ-Brief for the pooled group and the high-dose group relative to placebo. These differences reached statistical significance at several time points. For the pooled group, statistical significance compared with placebo was reached for all visits between Visit 3 and Visits 7 through 11 ($p<0.01$ at visit 3 and $\leq 0.04$ for visits 7 through 11, chi-square test obtained from repeated measures model). For the high-dose group, statistical significance compared with placebo was reached for Visits 3, 7, 9 and 11 ($p\leq 0.01$, 0.02, 0.01, and 0.01 for visits 3, 7, 9, and 11, respectively, chi-square test obtained from repeated measures model).

The primary efficacy variable, a change in CCQ-Brief from Visit 2 to Visit 12, was not significantly different for the pooled group compared with placebo. This was the expected outcome, as the Efficacy Evaluable data set in this small pilot study did not have sufficient statistical power because of the large number of patients who discontinued.

Reductions in cocaine use, as determined by measurement of the cocaine metabolite BE in urine, was a secondary endpoint in this study. All subjects tested positive for cocaine in urine samples at screening and were randomly assigned to treatment groups. As with craving measurements, differences between groups were seen in cocaine usage at baseline Visit 1, when 7 placebo subjects (78%) had a urine test positive for cocaine, compared to 5 subjects in the low-dose group (56%) and 3 subjects in the high-dose group (38%). However, the groups had comparable cocaine usage rates over the next several visits, suggesting that these differences probably reflect the variability of cocaine usage in this population rather than an inherent imbalance in the groups.

At end-of-study Visit 13, the number of subjects with a urine drug screen positive for cocaine in the pooled group (4 subjects; 24%) was significantly lower than in the placebo group (7 subjects; 78%; p=0.02, Fisher's Exact Test). At Visits 12 and 13, the number of subjects with a positive urine sample in the high-dose group was significantly lower than in the placebo group (p=0.02 and 0.01 for Visits 12 and 13, respectively, Fisher's Exact Test). In addition, at all visits after Visit 8, the percentage of subjects in the low-dose group with a urine sample positive for cocaine was less than in the placebo group. The mean number of visits per subject with a urine sample positive for cocaine during Visits 3-12 was significantly lower in both the high-dose group (3.9; p<0.05; Rank-Sum Test) and pooled group (4.5; p=0.04; Rank-Sum Test) compared with the placebo group (7.1).

After Visit 2, mean BE amounts in urine tended to show consistent reductions from screening in the low-dose and high-dose groups, whereas amounts of the metabolite were sometimes increased in the placebo group. Reductions in the high-dose group were always numerically greater than in the placebo group, and these differences were statistically significant at Visit 1 and Visit 6 (p<0.05; Rank-Sum Test).

No statistically significant differences were observed in HAM-A or HAM-D among the treatment groups, although a trend for a reduction emerged towards the end of the study in the high-dose group. No differences were observed in self-reported alcohol or cigarette consumption among groups, nor were differences seen in the results of drug screens for alcohol, nicotine metabolites or other drugs of abuse. However, at baseline ratings of anxiety and depression were low, subjects reported a low rate of alcohol consumption, and large variability in smoking rates was reported among groups. Therefore, the lack of significant differences among groups during the course of the study is not statistically meaningful.

Overall, administration of metyrapone and oxazepam at the doses used in this clinical study was well-tolerated, with a low proportion of severe adverse events and discontinuations due to adverse events. While this study is very small, and interpretation of the safety data is limited by the small numbers and high rates of subject discontinuations, there were no safety trends or unexpected findings. Two subjects discontinued from the study due to adverse events. One discontinued due to low serum cortisol at Visit 11, although the subject showed no signs or symptoms of low cortisol; serum cortisol <3 µg/dL was prospectively defined as a reason for discontinuation. The second subject discontinued due to irritability and nausea at Visit 3. Of note, the second subject continued to use cocaine during participation in the study. All 45 subjects reported at least 1 adverse event during the study. Only 6 of 109 events in the pooled group were considered to be probably or definitely related to study drug.

Changes in serum cortisol and ACTH concentrations are known effects of metyrapone. Trends of decreases in serum cortisol (high-dose group compared to placebo) and increases in serum ACTH (low- and high-dose groups compared to placebo) were seen. Eight subjects had serum cortisol concentrations below the lower limit of the reference range at one point during the study; however, review of concurrent adverse events did not reveal any adverse events consistent with signs or symptoms of low cortisol. Five of these 8 subjects completed the study, one discontinued early but had normal cortisol concentrations after the nadir, and 2 discontinued early and the last available serum cortisol concentration was low (Visit 5 for 1 subject, end-of-study Visit 13 for 1 subject). Both of these subjects were lost to follow-up and did not return for subsequent requested visits.

The assessment of safety is somewhat complicated in the study by the high discontinuation rate, with 23 subjects discontinuing prior to completing the study and 18 of these 23 subjects lost to follow-up. While this can sometimes raise concerns about general tolerability and the possibility that subjects are discontinuing for unreported adverse events, there is nothing to indicate that this is the case in this study. The high discontinuation rate is most likely related to characteristics of the study population.

In this pilot study of the clinical efficacy and safety of the combination of metyrapone and oxazepam in cocaine-dependent subjects, cocaine use was significantly lower at the end of treatment in the high-dose group compared to the placebo group, supporting the potential efficacy of the metyrapone/oxazepam combination. The high-dose combination also trended towards a reduction in craving during the study as measured by the CCQ-Brief. Both doses of the combination appeared to be well tolerated. These data are consistent with the results seen in animal models of cocaine dependence (Goeders et al., *Pharmacol. Biochem. Behav.* 91:181-189, 2008) and support the further exploration of this drug combination.

The primary prospectively-defined endpoint for this study was the change in CCQ-Brief from Visit 2 to Visit 12. Although a measure of cocaine use, such as self-reported cocaine use confirmed by urine benzoylecgonine, is typically chosen as the primary outcome measure in treatment studies of cocaine dependence (Anderson, *Drug Alcohol Depend.* 104:133-139, 2009), the CCQ-Brief seemed a reasonable choice as the primary endpoint since the proposed mechanism of action of the metyrapone/oxazepam combination in reducing the ability of stress-related environmental cues to stimulate drug use and relapse likely includes craving as an intermediary. However, since craving is a hypothetical construct, urine benzoylecgonine was also measured as a measure of actual cocaine use to more completely evaluate responses to the metyrapone/oxazepam combination. A post-hoc analysis of the CCQ-Brief data did reveal that the number of subjects evaluable for efficacy was too small for this to be a meaningful endpoint. Given the observed drug effect and placebo effect, 15 subjects were required per group to achieve 80% power. With only 8-9 subjects per group completing the study, the lack of a significant difference between the groups is not informative. In line with our study purpose, trends in the overall data and effects at specific time points were examined to provide insight into the activity of the drug combination.

Despite the small sample size, significant reductions in cocaine use and craving were observed by several measures. Cocaine craving was significantly reduced for the pooled group when compared to placebo for all visits between Visit 7 and Visit 11, while for the high-dose group, statistical significance compared with placebo was reached for Visits 7, 9 and 11 when controlling for the baseline assessment value. Similarly, the number of subjects treated with metyrapone/oxazepam who had cocaine-positive urines was significantly reduced at several time points. Furthermore, the mean total number of visits per subject with a urine sample positive for cocaine from Weeks 2 through 6 was significantly lower in both the high-dose and pooled groups when compared with the placebo group.

These statistically significant results were in the direction of a dose response, with significant responses obtained primarily in the high-dose group. Similar trends were seen throughout the data set, with reductions in both craving and cocaine use seen over time, and a trend towards reduced levels of BE in urine. These findings, even at those time points where the reductions were not statistically significant, show that the significant results were part of the overall trends of the data. The efficacy data as a whole are supportive of a meaningful effect of the metyrapone/oxazepam drug combination on cocaine use and craving.

Baseline differences between groups were seen in both cocaine use and craving. More placebo subjects than high-dose subjects had drug screens positive for cocaine at baseline, and baseline levels of craving were higher in the placebo group than in the high-dose group. These baseline differences were addressed in the statistical analyses, and the imbalance between groups does not interfere with the statistical findings of decreased cocaine use and craving in the drug-treated groups. However, it is possible that this difference may have contributed to the treatment benefit observed in the high-dose group. If the high-dose subjects had less severe disease (less craving and less cocaine use), they may have been more susceptible to a placebo effect, leading to a perceived treatment benefit from the drug. While this possibility cannot be ruled out entirely, it should be noted that no psychosocial support was provided in this study, and the placebo effect was expected to be negligible. This issue can only be fully addressed by testing the metyrapone/oxazepam drug combination in larger studies, which we believe this study supports.

No statistically significant differences were observed in HAM-A or HAM-D among the treatment groups, although a trend for a reduction emerged towards the end of the study in the high-dose group. The lack of differences among treatment groups is not surprising given the low baseline scores for these measures of anxiety and depression. The analysis of the combination treatment's effects on other drug use—alcohol and nicotine, specifically—was also likely limited by use patterns in this study. Alcohol consumption was low throughout the study in all treatment groups (i.e., about 1 drink per day). The high-dose group consumed a much lower mean number of cigarettes per day at baseline compared with the placebo group (i.e., approximately 60% of placebo), and across groups there was large variability in the number of cigarettes smoked per day.

Example 5

Effects of Metyrapol on Cocaine Self-Administration in Rats

We conducted the following experiment to explore the possibility that metyrapol would decrease cocaine self-administration in an animal model. Adult male Wistar rats were trained to respond under a 2-hour multiple, alternating schedule of food reinforcement and cocaine self-administration (fixed-ratio 4) during alternating 15-minute periods. Prior to testing, the rats were exposed to multiple saline substitution and food extinction probes. On test days, rats were pretreated 30 minutes prior to the start of the behavioral session with metyrapol (25, 50, 100, and 150 mg/kg, ip.) or vehicle. Subjects were initially trained and tested with 0.25 mg/kg/infusion of cocaine and, subsequently, with 0.125 and 0.5 mg/kg/infusion. Cocaine self-administration was dose dependently decreased at all three doses of cocaine. Food-maintained responding was not significantly affected except at the highest doses of metyrapol. These data support the hypothesis that metyrapol plays a role in the effects of metyrapone and suggests that metyrapol is useful in the treatment of cocaine addiction

What is claimed is:

1. A pharmaceutical composition comprising a first agent, wherein the composition is formulated for oral or topical administration to a patient,
    wherein the first agent is metyrapone or metyrapol, and
    wherein the first agent is conjugated to an agent that facilitates movement across the blood-brain barrier.

2. The pharmaceutical composition of claim 1, further comprising a second pharmaceutically active agent,
    wherein the second pharmaceutically agent increases the expression or activity of GABA (gamma-aminobutyric acid), is a GABA mimic or inhibits GABA metabolism.

3. The pharmaceutical composition of claim 2, wherein the second pharmaceutically active agent is a benzodiazepine.

4. The pharmaceutical composition of claim 2, wherein the composition is present in a unit dosage form.

5. The pharmaceutical composition of claim 1, wherein the first agent is present in an amount insufficient to reduce plasma levels of cortisol in the patient.

6. The pharmaceutical composition of claim 1, further comprising an efflux inhibitor that helps maintain metyrapol levels in the brain, wherein (a) the efflux inhibitor is an inhibitor of ABC efflux transport mechanisms; or (b) the efflux inhibitor is an excipient comprising one or more of: polyethylene glycol, glycerin, and gelatin.

7. The pharmaceutical composition of claim 6, wherein the inhibitor of ABC efflux transport mechanism is an inhibitor of P-glycoprotein (Pgp).

8. The pharmaceutical composition of claim 1, further comprising an agent that transiently manipulates the blood-brain barrier.

9. The pharmaceutical composition of claim 8, wherein the agent that transiently manipulates the blood-brain barrier is mannitol or bradykinin.

10. The pharmaceutical composition of claim 3, wherein the benzodiazepine is selected from the group consisting of: oxazepam, chlordiazepoxide, diazepam and alprazolam.

11. The pharmaceutical composition of claim 2, wherein the second pharmaceutically active agent is selected from the group consisting of: a benzodiazepine, mirtazapine, atomoxetine, gabapentin, muscimol, baclofen, progabide, pregabalin, riluzole, vigabatrin, valproic acid, tiagabine, lamotrigine, phenytoin, carbamazepine, topiramate, a barbiturate, carisoprodol, chloral hydrate, glutethimide, L-theanine, kava, methaqualone, neuroactive steroids, z-drugs, propofol, scullcap, valerian, gamma-butyrolactone, gamma-hydroxybutyric acid, phenibut, deramciclane, hyperforin, gabaculine, phenelzine, valproate, vigabatrin, lemon balm (*Melissa officinalis*), GABA, L-glutamine, picamilon, and tetanospasmin.

12. The pharmaceutical composition of claim 2, further comprising a third agent that targets the sympathetic nervous system.

* * * * *